(12) United States Patent
Kuyler et al.

(10) Patent No.: US 11,554,021 B2
(45) Date of Patent: Jan. 17, 2023

(54) EXPANDING INTERBODY IMPLANT AND METHOD

(71) Applicant: WARSAW ORTHOPEDIC INC., Warsaw, IN (US)

(72) Inventors: Adriaan J. Kuyler, Saint Augustine, FL (US); Anthony J. Melkent, Germantown, TN (US); Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/938,016

(22) Filed: Jul. 24, 2020

(65) Prior Publication Data

US 2022/0023061 A1    Jan. 27, 2022

(51) Int. Cl.
*A61F 2/44* (2006.01)
*A61F 2/30* (2006.01)

(52) U.S. Cl.
CPC .. *A61F 2/4425* (2013.01); *A61F 2002/30538* (2013.01); *A61F 2002/30556* (2013.01); *A61F 2002/443* (2013.01)

(58) Field of Classification Search
CPC ...... A61F 2/4455; A61F 2/447; A61F 2/4425; A61F 2/443
See application file for complete search history.

(56) References Cited

U.S. PATENT DOCUMENTS

| | | | | |
|---|---|---|---|---|
| 8,366,777 | B2* | 2/2013 | Matthis | A61F 2/4425 |
| | | | | 623/17.16 |
| 9,216,095 | B2* | 12/2015 | Glerum | A61F 2/4611 |
| 9,962,272 | B1* | 5/2018 | Daffinson | A61F 2/4611 |
| 10,085,846 | B2* | 10/2018 | Grotz | A61F 2/4611 |
| 11,065,127 | B1* | 7/2021 | Lentner | A61F 2/447 |
| 2017/0128226 | A1* | 5/2017 | Faulhaber | A61F 2/30767 |
| 2019/0105178 | A1* | 4/2019 | May et al. | A61F 2/30767 |
| 2020/0281741 | A1* | 9/2020 | Grotz | A61F 2/4455 |

* cited by examiner

*Primary Examiner* — Tessa M Matthews
(74) *Attorney, Agent, or Firm* — Sorell, Lenna & Schmidt LLP

(57) ABSTRACT

A device includes a core defining first and second female threads. A first member includes a first body and a first drive screw coupled to the first body, the first drive screw being configured to engage the first female thread. A second member includes a second body and a second drive screw coupled to the second body, the second drive screw being configured to engage the second female thread. A first plate is coupled to the core and the first body. The first plate includes a first vertebral engaging surface. A second plate is coupled to the core and the second body. The second plate includes a second vertebral engaging surface. The drive screws are configured to independently rotate relative to the core to pivot the first plate relative to the core and to alter a distance between the first vertebral engaging surface and the second vertebral engaging surface.

19 Claims, 13 Drawing Sheets

EXPANDING INTERBODY IMPLANT AND METHOD

TECHNICAL FIELD

The present disclosure generally relates to medical devices, systems and methods for the treatment of musculoskeletal disorders, and more particularly to an expandable interbody implant system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

In one embodiment, in accordance with the principles of the present disclosure, a device to space apart vertebral members includes a core extending along a longitudinal axis between opposite proximal and distal ends. The core defines a first female thread and a second female thread. A first member comprises a first body and a first drive screw coupled to the first body. The first drive screw has a first male thread configured to engage the first female thread. A second member comprises a second body and a second drive screw coupled to the second body. The second drive screw has a second male thread configured to engage the second female thread. A first plate is coupled to the core and the first body. The first plate comprises a first vertebral engaging surface. A second plate is coupled to the core and the second body. The second plate comprises a second vertebral engaging surface. The drive screws are configured to independently rotate relative to the core to pivot the first plate relative to the core and to alter a distance between the first vertebral engaging surface and the second vertebral engaging surface.

In one embodiment, in accordance with the principles of the present disclosure, a device to space apart vertebral members includes a core extending along a longitudinal axis between opposite proximal and distal ends. The core defines a first female thread and a second female thread. A first member comprises a first body and a first drive screw coupled to the first body. The first body includes a first ramp. The first drive screw has a first male thread configured to engage the first female thread. A second member comprises a second body and a second drive screw coupled to the second body. The second body comprises a plurality of spaced apart first inclined surfaces. The second drive screw has a second male thread configured to engage the second female thread. A first plate is coupled to the core and the first body. The first plate comprises a first vertebral engaging surface and a second ramp. A second plate is coupled to the core and the second body. The second plate comprises a second vertebral engaging surface and a plurality of spaced apart second inclined surfaces. The drive screws are configured to independently rotate relative to the core to move the second ramp along the first ramp to pivot the first plate relative to the core and to slide the second inclined surfaces along the first inclined surfaces to alter a distance between the first vertebral engaging surface and the second vertebral engaging surface.

In one embodiment, in accordance with the principles of the present disclosure, a device to space apart vertebral members includes a core extending along a longitudinal axis between opposite proximal and distal ends. The core defines a first female thread and a second female thread that is spaced apart from the first female thread. The first female thread has a major diameter that is less than a major diameter of the second female thread. A first member comprises a first body and a first drive screw coupled to the first body. The first drive screw has a first male thread configured to engage the first female thread. A second member comprises a second body and a second drive screw coupled to the second body. The second drive screw has a second male thread configured to engage the second female thread. The first drive screw is coaxial with the second drive screw. The second drive screw comprises a bore that is coaxial with a central longitudinal axis defined by the first drive screw such that an instrument can be positioned through the bore and into a socket of the first drive screw. A first plate is coupled to the core and the first body. The first plate comprises a first vertebral engaging surface. A second plate is coupled to the core and the second body. The second plate comprises a second vertebral engaging surface. The drive screws are configured to independently rotate relative to the core to pivot the first plate relative to the core and to alter a distance between the first vertebral engaging surface and the second vertebral engaging surface. Rotation of first drive screw relative to the core translates the first body along the longitudinal axis such that the first plate pivots relative to the core to move the device from a first orientation in which the first vertebral engaging surface extends parallel to the longitudinal axis and the second vertebral engaging surface to a second orientation in which the first vertebral engaging surface extends at an acute angle relative to the longitudinal axis and the second vertebral engaging surface. Rotation of the first drive screw relative to the core in an opposite second rotational direction translates the first body along the longitudinal axis in an opposite second direction such that the first plate pivots relative to the body to move the device from the second orientation to the first orientation. Rotation of second drive screw relative to the core in a first rotational direction translates the second body relative to the core along the longitudinal axis in a first longitudinal direction to move the device from a first configuration in which the vertebral engaging surfaces are spaced apart a first distance from one another to a second configuration in which the vertebral engaging surfaces are spaced apart a second distance from one another. The second distance is greater than the first distance. Rotation of the second drive screw relative to the core in an opposite second rotational direction translates the second body along the longitudinal axis in an opposite second longitudinal direction to move the device from the second configuration to the first configuration. The second body comprises inclined surfaces that slide along inclined surfaces of the second plate as the second body translates relative to the core along the longitudinal axis to move the device from the first configuration to the second configuration. The second plate comprises a plurality of rails each extending perpendicular to the longitudinal axis and the core comprises a plurality of slots each extending perpendicular to the longitudinal axis. The rails each translate within one of the slots as the device moves between the first configuration and the second configuration.

BRIEF DESCRIPTION OF THE DRAWINGS

The present disclosure will become more readily apparent from the specific description accompanied by the following drawings, in which.

DETAILED DESCRIPTION

Figure 1:
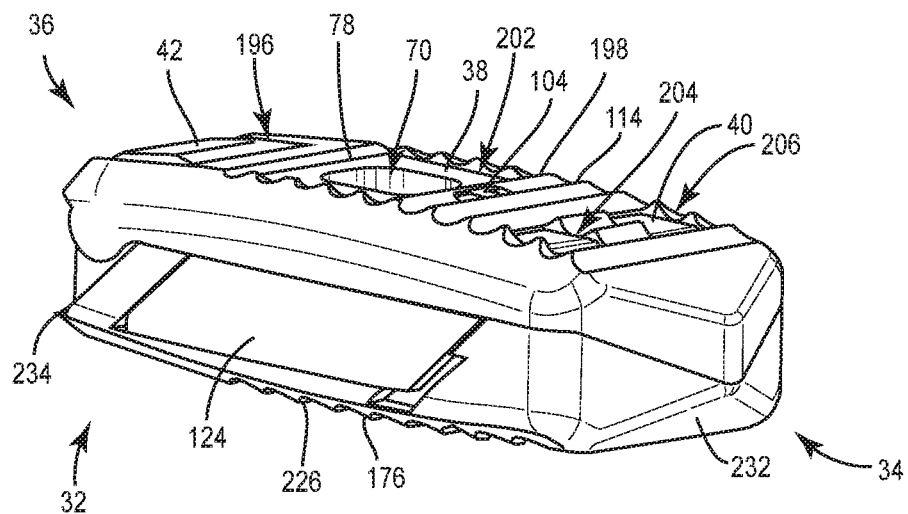
FIG. 1 is a perspective view of one embodiment of an implant of a system in accordance with the principles of the present disclosure.

The exemplary embodiments of an expandable interbody implant system and related methods of use disclosed herein are discussed in terms of medical devices for the treatment of musculoskeletal disorders and more particularly, in terms of an expandable interbody implant system and related methods for treating a vertebral column. It is envisioned that the implant system may provide, for example, fusion, decompression, restoration of sagittal balance and resistance of subsidence into tissue, such as, for example, surfaces of vertebral endplates.

In some embodiments, the expandable interbody implant of the system disclosed herein is used to achieve implanted geometries that would otherwise be impossible or challenging to insert with minimal morbidity. The expandable interbody implant allows for expansion in two, independently controlled manners. One component increases the overall height of the implant (parallel expansion), while another manipulates the angle of the end plates of the implant.

In some embodiments, the independent parallel and angular expansion are both infinitely adjustable (within the prescribed range). In some embodiments, the implant is configured to cover all clinically needed size combinations (angles and heights) with a single implant. In some embodiments, two separate drivers can control each drive screw for separated expansion. In some embodiments, a single driver can be made that will advance both drive screws simultaneously. In some embodiments, the implant is post-packed with bone graft.

It is envisioned that the implant provides the ability to closely match a patient's disc geometry since any height and angle combination of the implant is attainable. Since only one or a few different size implants would be needed to match any disc geometry, manufacturing costs could be significantly reduced, leaning out production and logistics. There is also a reduced number of instruments that would be required for implantation of the implant(s). The system of the present disclosure may also prevent the need to have trials or distractors because of the capabilities of the implant of the present disclosure, which would also reduce the traditional surgical steps.

In some embodiments, the expandable interbody implant of the system disclosed herein includes proximal and distal drive screws. The proximal drive screw controls the parallel expansion and is larger and hollow through the center to allow for a driver of the distal drive screw to pass through as well as the insertion of graft material after implantation and expansion. The distal drive screw controls the angular expansion and is in-line with the proximal screw. Both drive screws are in-line with the inserter.

In some embodiments, the expandable interbody implant of the system disclosed herein includes a first part that is coupled to the distal drive screw and a second part that is coupled to the proximal drive screw. The first part is involved with angling a top member of the implant relative to a core of the implant. The second part is involved with moving the top member toward and away from a bottom member of the implant. In some embodiments, the first part has a raised section that engages a slot on the top member in order to provide stabilization. In some embodiments, the first part has a slot for disposal of a groove of the top member in order to provide stabilization. In some embodiments, the top member attaches to the core by a pin connection. In some embodiments, the top member attaches to the core by reliefs that are cut into the core such that the cylinders are machined directly into the top member. The second part can be keyed to engage the proximal drive screw or can be attached to the proximal drive screw by pin, collet, or snap ring.

In some embodiments, the proximal drive screw achieves parallel expansion by causing distal inclined surfaces of the second part to act on distal inclined surfaces of the bottom member. In some embodiments, the proximal drive screw achieves parallel collapsing by causing proximal inclined surfaces of the second part to act on proximal inclined surfaces of the bottom member. In some embodiments, the proximal drive screw attaches to the second part as a collet, which is prevented from collapsing by the driver when the driver is inserted to advance or retreat the screw. In some embodiments, the proximal drive screw is attached to the second part by a snap ring or is pinned to the second part. In some embodiments, the bottom member has tabs that engage the second part to prevent splaying of the second part. In some embodiments, the core has slots that guide rails of the bottom member. In some embodiments, the second part includes an opening that is adjacent to an opening of the core and a cap is included to couple the second part to the core. In some embodiments, the core has a center opening and no cap is required because the structure is held together by the rails of the bottom member.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed expandable interbody implant may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The expandable interbody implant of the present disclosure may also be alternatively employed with procedures for treating the lumbar, cervical, thoracic and pelvic regions of a spinal column. The expandable interbody implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an expandable interbody implant and related methods of employing the expandable interbody implant in accordance with the principles of the present disclosure. Alternate embodiments are also disclosed. Reference will now be made in detail to the exemplary embodiments of the present disclosure, which are illustrated in the accompanying figures. Turning now to FIGS. 1-23, there is illustrated components of an interbody implant system 30 in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (for example, Nitinol, super elastoplastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyether ketone ketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polylactide, polyglycolide, polytyrosine carbonate, polycaprolactone and their combinations. Various components of system 30 may be fabricated from material composites, including the above materials, to achieve various desired characteristics such as strength, rigidity, elasticity, flexibility, compliance, biomechanical performance, durability and radiolucency or imaging preference. The components of system 30, individually or collectively, may also be fabricated from a heterogeneous material such as a combination of two or more of the above-described materials.

System 30 can be employed in fusion and fixation procedures, for example, for patients suffering from a spinal disorder to provide height restoration between vertebral bodies, decompression, restoration of sagittal balance and/or resistance of subsidence into vertebral endplates. The components of system 30 may be monolithically formed, integrally connected or include fastening elements and/or instruments, for example, as described herein.

Figure 12:
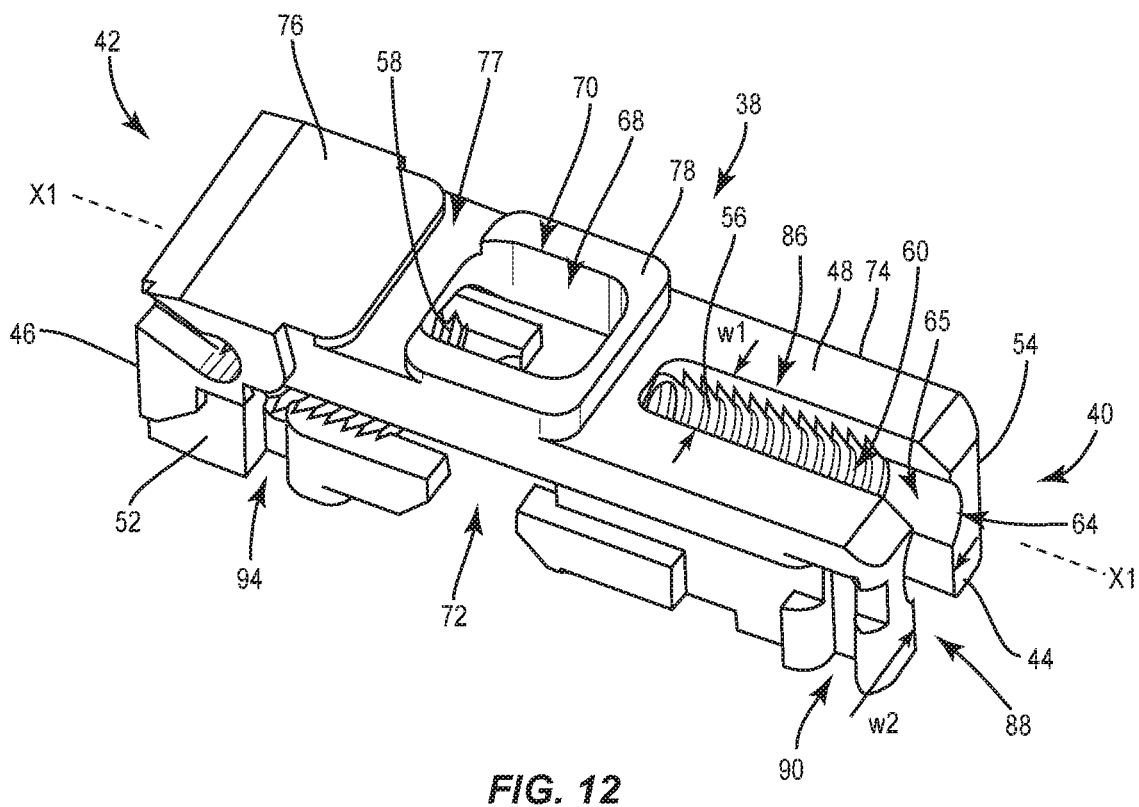
FIG. 12 is a perspective view of a component of the implant shown in FIG. 1.
Figure 13:
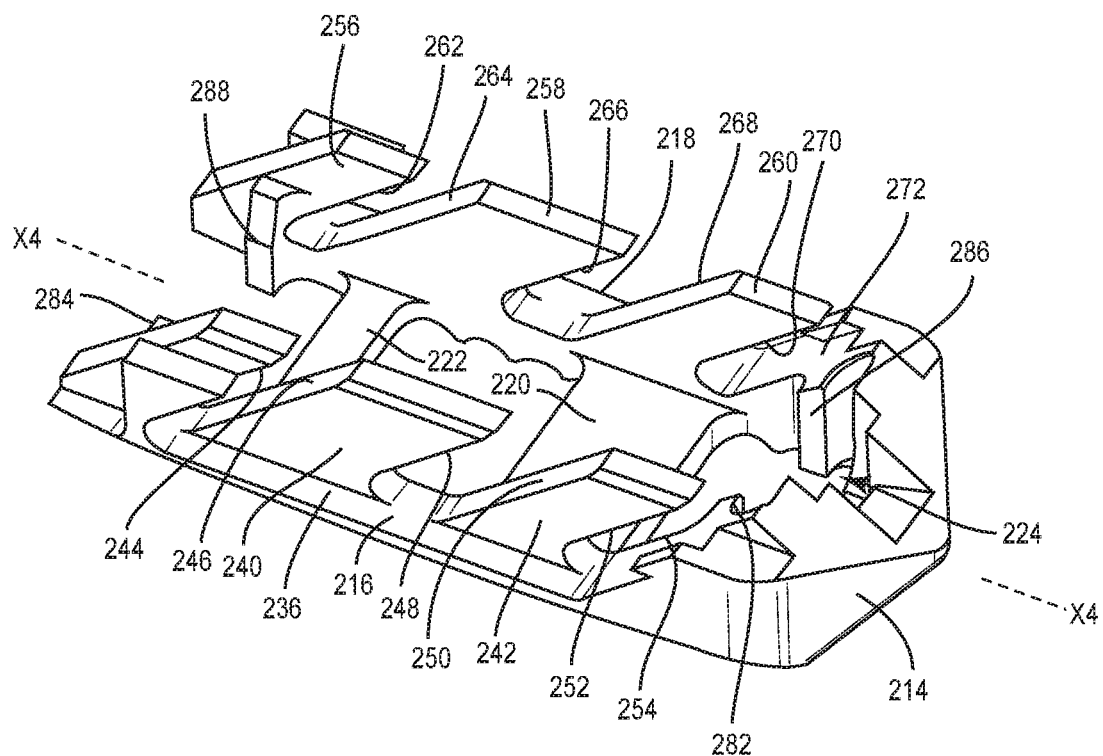
FIG. 13 is a perspective view of a component of the implant shown in FIG. 1.
Figure 14:
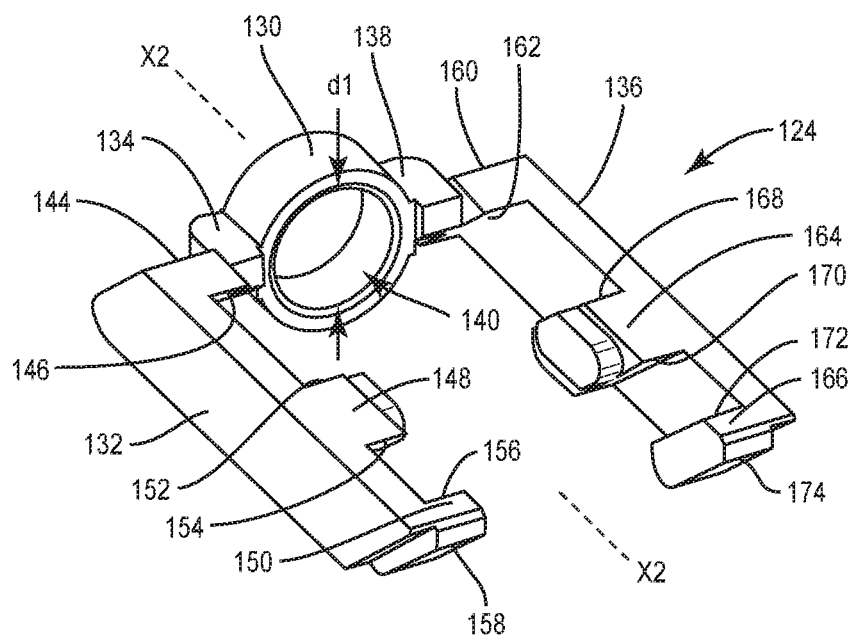
FIG. 14 is a perspective view of a component of the implant shown in FIG. 1.
Figure 15:
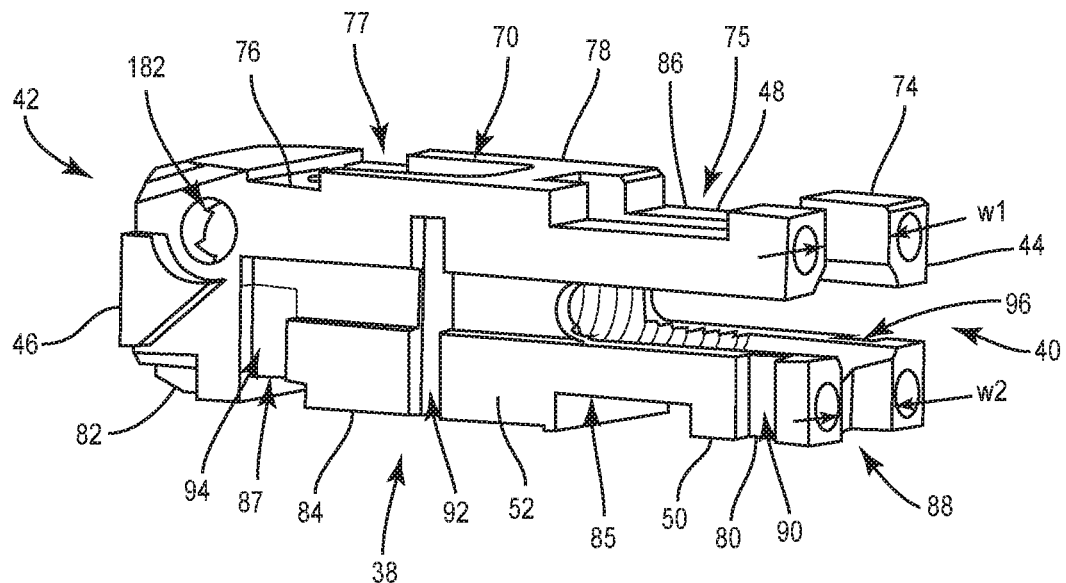
FIG. 15 is a perspective view of a component of the implant shown in FIG. 1.
Figure 16:
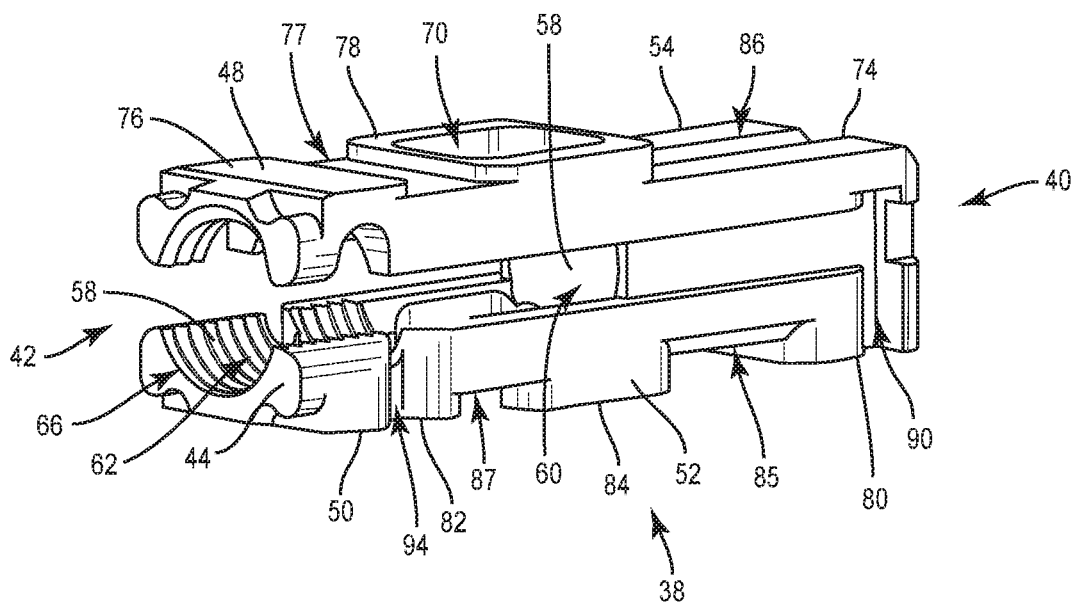
FIG. 16 is a perspective view of a component of the implant shown in FIG. 1.

System 30 includes an implant, such as, for example, an intervertebral implant 32. Implant 32 is configured for separately controlled parallel and angled expansion, as discussed herein. Implant 32 includes a distal end 34 and an opposite proximal end 36. Implant 32 comprises a core member or component, such as, for example, a core 38. Core 38 extends along a central longitudinal axis X1 between a distal end 40 and an opposite proximal end 42. End 40 includes an end wall 44 and end 42 includes an end wall 46 opposite wall 44. Core 38 includes a top wall 48 extending continuously from wall 44 to wall 46 and a bottom wall 50 opposite wall 48. Core 38 further includes opposite side walls 52, 54 between wall 44 and wall 46 and between wall 48 and wall 50. Inner surfaces of walls 48, 50, 52, 54 define a female thread 56 and a female thread 58. Thread 56 defines a passageway 60 and thread 58 defines a passageway 62. Wall 44 defines an opening 64 that is in communication with passageway 60 and wall 46 defines an opening 66 that is in communication with passageway 62. Thread 56 has a major diameter that is less than a major diameter of thread 58. Passageway 60 has a maximum diameter that is less than a maximum diameter of passageway 62. In some embodiments, passageways 60, 62 are coaxial with axis X1. In some embodiments, passageway 60 and/or passageway 62 may be disposed at alternate orientations, relative to axis X1, such as, for example, transverse and/or other angular orientations such as acute or obtuse and/or may be offset or staggered. In some embodiments, core 38 includes a non-threaded bore 65 positioned between passageway 60 and opening 64, as best shown in FIG. 12. In some embodiments, bore 65 has a maximum diameter that is less than the maximum diameter of passageway 60 to prevent a drive screw that is threaded with thread 56 to move through opening 64, as discussed herein.

Thread 56 is spaced apart from thread 58 by a gap, such as, for example, a cavity 68 configured for disposal of material, such as, for example, bone graft material. Wall 48 defines an aperture 70 and wall 50 defines an aperture 72. Apertures 70, 72 are each in communication with cavity 68 and are configured to introduce bone graft or other material into cavity 68 after a height and/or angle of implant 32 has been selectively adjusted, as discussed herein. In some embodiments, aperture 70 is coaxial with aperture 72. In some embodiments, cavity 68 is non-threaded and/or free of threads. In some embodiments, aperture 70 and/or aperture 72 can have various shape configurations, such as, for example, circular, oval, oblong, square, polygonal, irregular, uniform, non-uniform, variable and/or tapered. In some embodiments, aperture 70 and/or aperture 72 may be disposed at alternate orientations, relative to axis X1, such as, for example, transverse, perpendicular and/or other angular orientations such as acute or obtuse, co-axial and/or may be offset or staggered.

Figure 5:
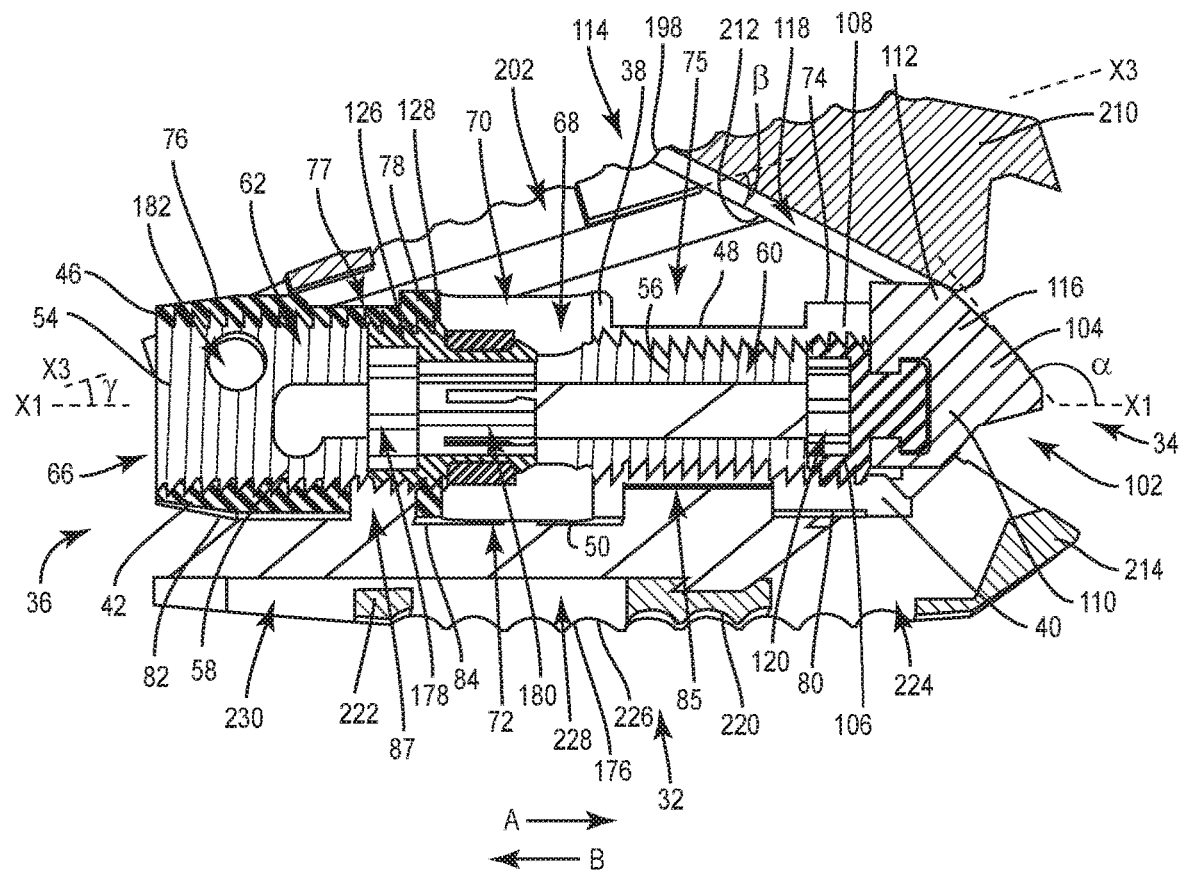
FIG. 5 is a side, cross-sectional view of the implant shown in FIG. 1.
Figure 6:
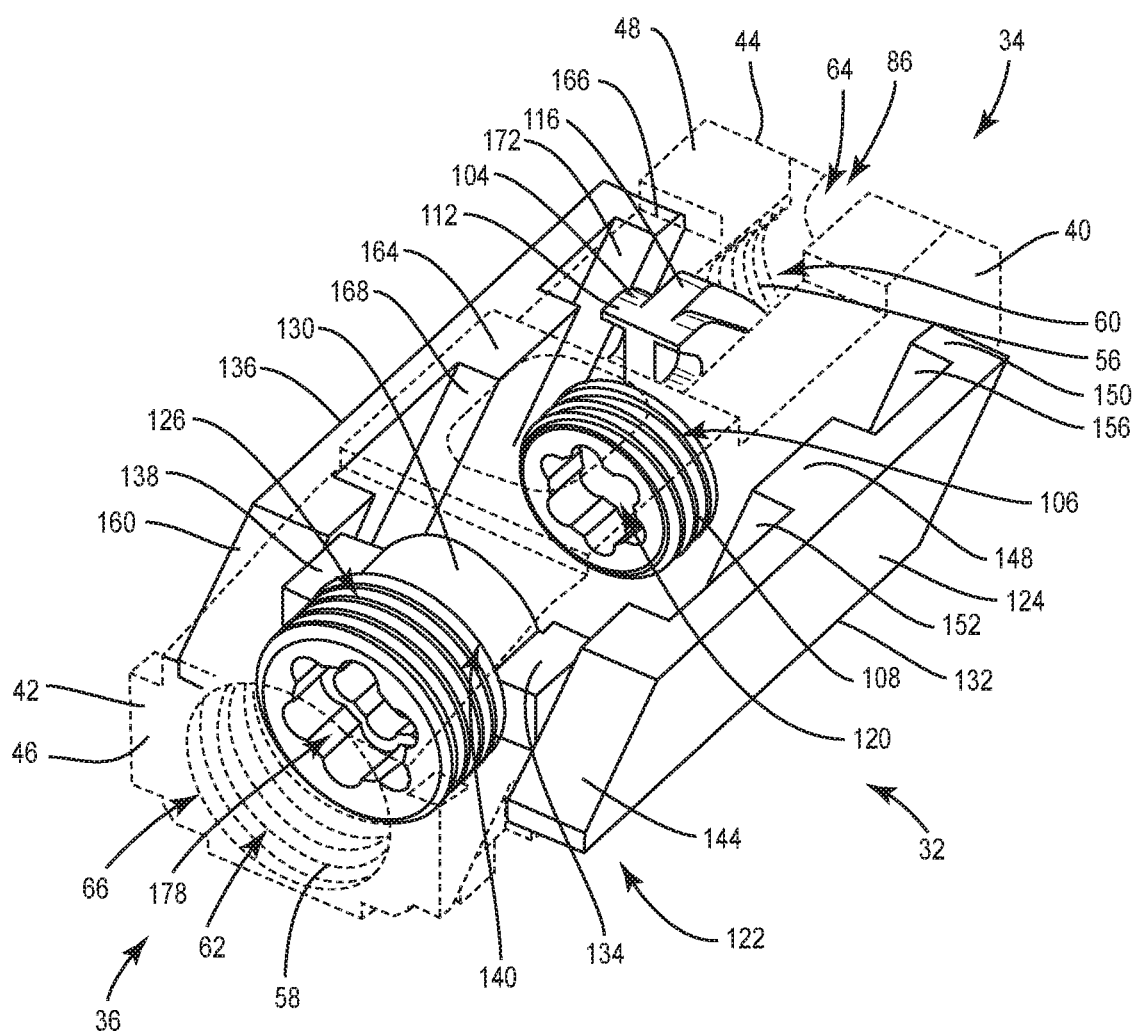
FIG. 6 is a perspective view, in part phantom, of components of the implant shown in FIG. 1.
Figure 7:
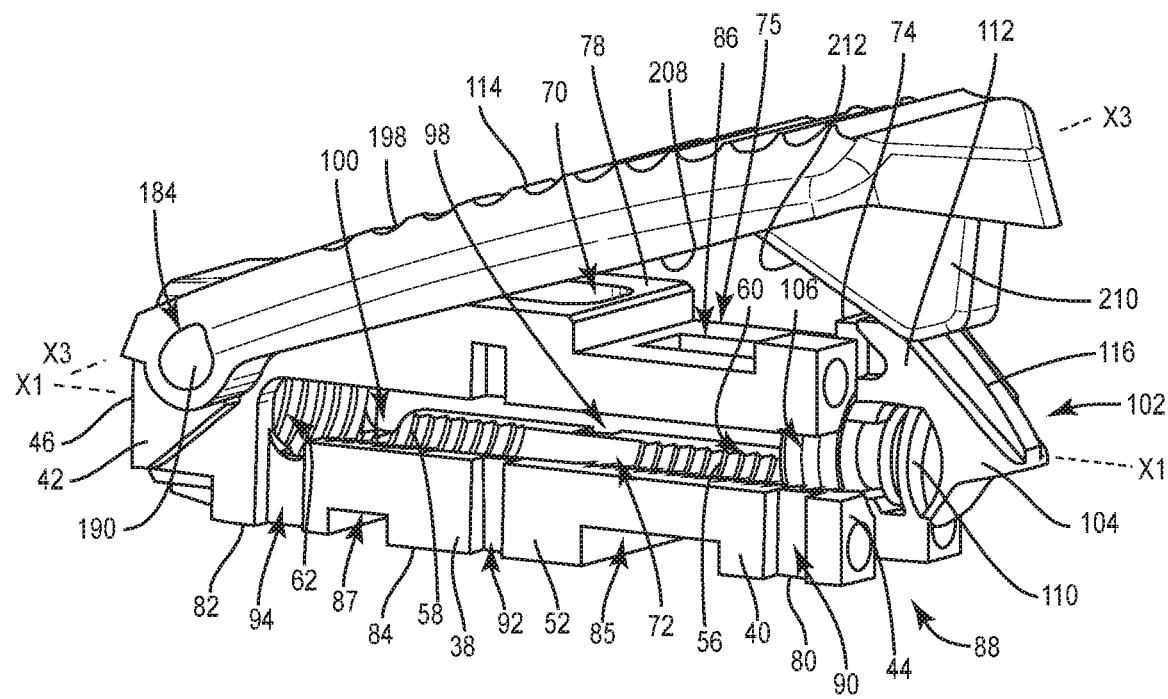
FIG. 7 is a perspective view of components of the implant shown in FIG. 1.

Wall 48 includes end sections 74, 76 and a middle section 78 positioned between section 74 and section 66 such that section 76 is spaced apart from section 74 by section 78, as best shown in FIG. 5. Wall 48 includes a recess 75 between section 74 and section 78 and a recess 77 between section 76 and section 78. Section 78 is configured for disposal in a recess of a component of implant 32 prior to angular expansion of implant 32, as discussed herein. In some embodiments, section 78 encircles aperture 70. That is, section 78 extends three hundred and sixty degrees about aperture 70. In some embodiments, section 78 extends around only a portion of aperture 70, such as, for example, around three out of four sides of aperture 70, as shown in FIG. 12. In some embodiments, section 78 can have various shape configurations, such as, for example, circular, oval, oblong, square, polygonal, irregular, uniform, non-uniform, variable and/or tapered.

Wall 50 includes end sections 80, 82 and a middle section 84 positioned between section 80 and section 82 such that section 84 is spaced apart from section 80 by section 82, as best shown in FIG. 5. Wall 50 includes a recess 85 between section 80 and section 84 and a recess 87 between section 82 and section 84. Section 84 is configured for disposal in a recess of a component of implant 32 prior to angular expansion of implant 32, as discussed herein. In some embodiments, section 84 encircles aperture 72. That is, section 84 extends three hundred and sixty degrees about aperture 72. In some embodiments, section 84 extends around only a portion of aperture 72, such as, for example, around three out of four sides of aperture 72. In some embodiments, section 84 can have various shape configurations, such as, for example, circular, oval, oblong, square, polygonal, irregular, uniform, non-uniform, variable and/or tapered.

Core 38 includes a slot 86 that extends through wall 48 and is in communication with passageway 60. Slot 86 extends parallel to axis X1 along an entire length of slot 86. Slot 86 is configured for sliding disposal of a component of implant 32 as an angle of implant 32 is selectively increased and decreased, as discussed herein. Slot 86 extends through wall 44 and has a width w1, as shown in FIG. 12. In some embodiments, width w1 is uniform along the entire length of slot 86. In some embodiments, width w1 tapers toward wall 44. In some embodiments, width w1 tapers toward section 78.

Core 38 includes a slot 88 that extends through wall 50 and is in communication with passageway 60. Slot 88 extends parallel to axis X1 along an entire length of slot 88. Slot 88 is configured for sliding disposal of a component of implant 32 as an angle of implant 32 is selectively increased and decreased, as discussed herein. Slot 88 extends through wall 44 and has a width w2, as shown in FIG. 12. In some embodiments, width w2 is uniform along the entire length of slot 88. In some embodiments, width w2 tapers toward wall 44. In some embodiments, width w2 tapers toward section 78. In some embodiments, width w2 is equal to width w1. In some embodiments, width w2 is greater than width w1. In some embodiments, width w2 is less than width w1.

Wall 52 includes spaced apart slots, such as, for example, grooves 90, 92, 94 and wall 54 includes spaced apart grooves 96, 98, 100 wherein groove 96 is opposite groove 90, groove 98 is opposite groove 92 and groove 100 is opposite groove 94. Groove 96 is the same or similar to groove 90. Groove 98 is the same or similar to groove 92. Groove 100 is the same or similar to groove 94. Grooves 90, 92, 94, 96, 98, 100 are configured for sliding disposal of rails of a component of implant 32 as the height of implant 32 is selectively increased and/or decreased, as discussed herein. Grooves 90, 92, 94, 96, 98, 100 extend parallel to one another. Grooves 90, 92, 94, 96, 98, 100 extend perpendicular to axis X1. In some embodiments, at least one of grooves 90, 92, 94, 96, 98, 100 may be disposed at alternate orientations, relative to axis X1, such as, for example, transverse, and/or other angular orientations such as acute or obtuse and/or may be offset or staggered.

Figure 17:
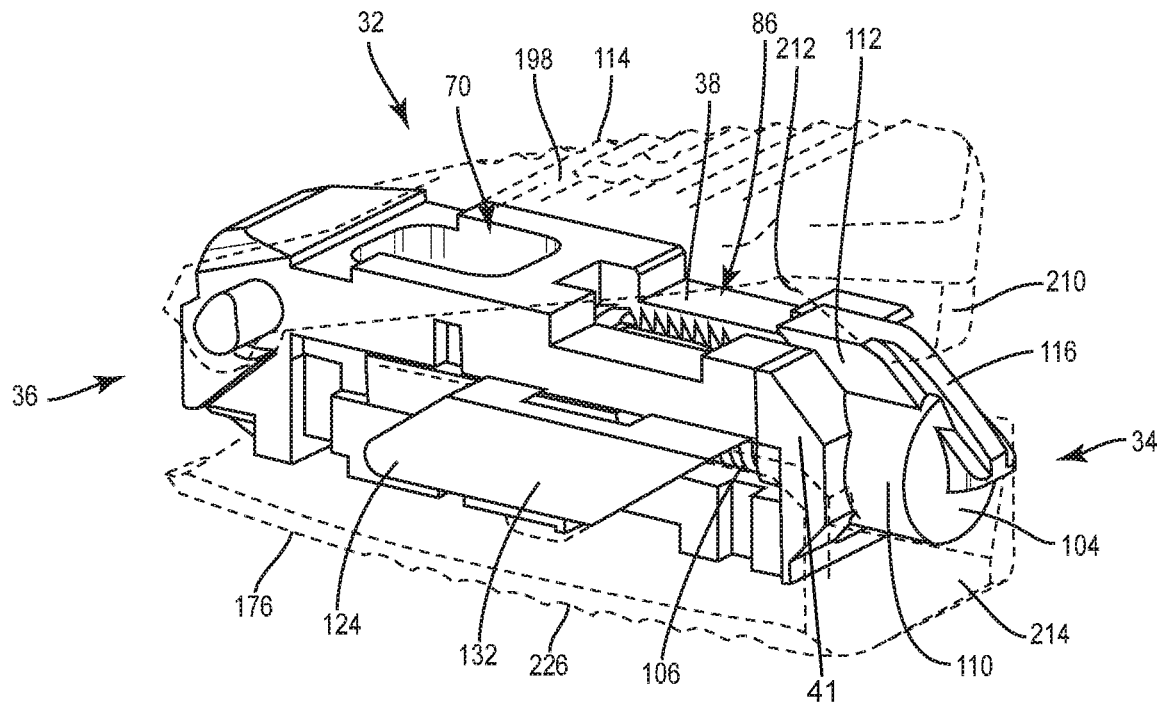
FIG. 17 is a perspective view, in part phantom, of the implant shown in FIG. 1.
Figure 18:
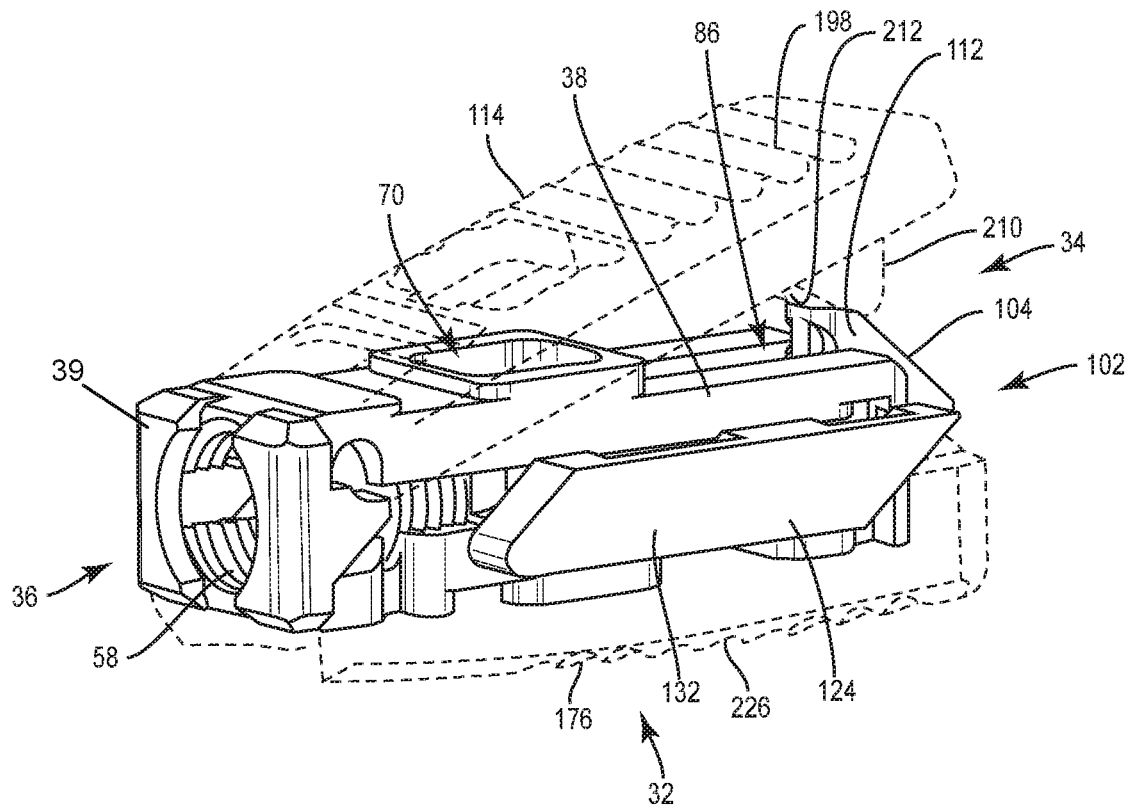
FIG. 18 is a perspective view, in part phantom, of the implant shown in FIG. 1.
Figure 19:
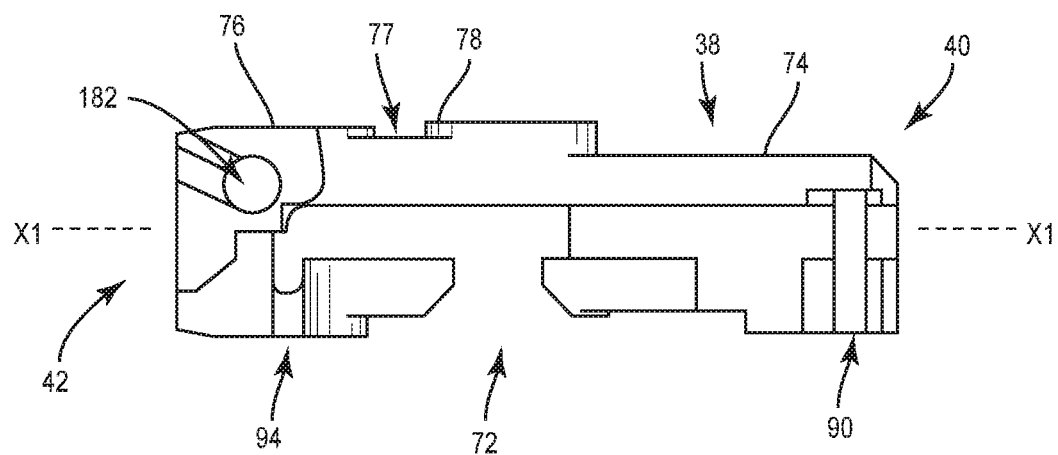
FIG. 19 is a side view of components of the implant shown in FIG. 1

It is envisioned that core 38 can have different designs without changing the function of core 38 and/or the operation of implant 32. In particular, it is envisioned that core 38 can include different designs that include openings at different areas of core 38. For example, in some embodiments, implant 32 includes a bottom open version of core 38, shown in FIG. 12, that includes aperture 72 to allow implant 32 to be assembled without a cap. That is, implant 32 that includes the embodiment of core 38 shown in FIG. 12 is assembled without a cap such that aperture 72 remains open when implant is assembled. In some embodiments, implant 32 includes an open version of core 38, shown in FIG. 15, that includes an opening similar to opening 64 between slots 86, 88 that is in communication with passageway 60 and configured to allow implant 32 to be assembled with a cap 41 that closes the opening when implant 32 is assembled, as shown in FIG. 17. In some embodiments, implant 32 includes an open version of core 38, shown in FIG. 16, that includes an opening 66 configured to allow implant 32 to be assembled with a cap 39 that closes opening 66 when implant 32 is assembled, as shown in FIG. 18. The various designs of core 38 thus allow a medical practitioner various option to assemble implant 32. It is envisioned that cap 39 and/or cap 41 can be connected with core by welding, adhesive, press fit, or other fixation techniques.

Implant 32 includes a distal member, such as, for example, a member 102. Member 102 comprises a distal body 104 and a distal drive screw 106 that is coupled to body 104. Member 102 is configured to translate relative to core 38 along axis X1 in opposite directions to selectively increase and decrease an angle of implant 32, as discussed herein. Screw 106 is configured for disposal in passageway 60 and includes a male thread 108 configured to mate with thread 56 such that rotation of screw 106 relative to core 38 about axis X1 in a first rotational direction, such as, for example, clockwise will translate screw 106 along axis X1 in a first axial direction, such as, for example, the direction shown by arrow A in FIG. 5 and rotation of screw 106 relative to core 38 about axis X1 in an opposite rotational direction, such as, for example, counterclockwise will translate screw 106 along axis X1 in an opposite section axial direction, such as, for example, the direction shown by arrow B in FIG. 5.

In some embodiments, body 104 is keyed to engage screw 106 such that translation of screw 106 relative to core 38 along axis X1 in the direction shown by arrow A in FIG. 5 also translates body 104 relative to core 38 along axis X1 in the direction shown by arrow A in FIG. 5 and translation of screw 106 relative to core 38 along axis X1 in the direction shown by arrow B in FIG. 5 also translates body 104 relative to core 38 along axis X1 in the direction shown by arrow B in FIG. 5. In some embodiments, screw 106 is coupled to body 104 by a pin. In some embodiments, screw 106 is coupled to body 104 by a collet. In some embodiments, screw 106 is coupled to body 104 by a snap ring. In some embodiments, screw 106 can be variously coupled to body 104, such as, for example, monolithic, integral connection, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts.

Body 104 includes an engagement portion 110 configured for engagement with screw 106 to couple screw 106 to body 104, as discussed herein. Portion 110 is coaxial with axis X1 when screw 106 is positioned in passageway 60 and thread 108 engages thread 56 and is movable within passageway 60 as screw 106 translates relative to core 38 along axis X1. Body 104 includes a wall 112 coupled to portion 110. Wall 112 extends at an angle α relative to axis X1 when screw 106 is positioned in passageway 60 and thread 108 engages thread 56 and is movable within slot 86 as screw 106 translates relative to core 38 along axis X1, as shown in FIG. 5. Wall 112 is configured to engage a top member or component, such as, for example, a plate 114 of implant 32 to selectively increase and decrease an angle of plate 114 relative to axis X1, as discussed herein. In some embodiments, body 104 includes a flange 116 that extends outwardly from wall 112 and is configured for disposal in a slot 118 of plate 114 as member 102 translates along axis X1 in opposite directions to selectively increase and decrease an angle of plate 114 relative to axis X1. In some embodiments, flange 116 extends at an angle α relative to axis X1 when screw 106 is positioned in passageway 60 and thread 108 engages thread 56 and is movable within slot 86 as screw 106 translates relative to core 38 along axis X1. In some embodiments, body 104 includes a slot that extends into wall 112 and is configured for disposal of a flange of plate 114 as member 102 translates along axis X1 in opposite directions to selectively increase and decrease an angle of plate 114 relative to axis X1. In some embodiments, angle α is an angle between about 120 degrees and about 179 degrees. In some embodiments, angle α is an angle between about 130 degrees and about 179 degrees. In some embodiments, angle α is an angle between about 140 degrees and about 179 degrees. In some embodiments, angle α is an angle between about 150 degrees and about 179 degrees. In some embodiments, angle α is an angle between about 160 degrees and about 179 degrees.

Screw 106 includes a socket 120 configured for disposal of a bit of a driver configured to rotate screw 106 relative to core 38 about axis X1 in opposite directions, as discussed herein. In some embodiments, socket 120 includes a hexalobe cross-sectional configuration configured for engagement with a bit of a driver having a hexalobe cross-sectional configuration to rotate screw 106. However, it is envisioned that socket 120 may include a square, triangular, polygonal, star cross sectional configuration configured engage a correspondingly shaped bit of a driver.

Implant 32 includes a proximal member, such as, for example, a member 122. Member 122 comprises a distal body 124 and a distal drive screw 126 that is coupled to body 124. Member 122 is configured to translate relative to core 38 along axis X1 in opposite directions to selectively increase and decrease a height of implant 32, as discussed herein. Screw 126 is configured for disposal in passageway 62 and includes a male thread 128 configured to mate with thread 58 such that rotation of screw 126 relative to core 38 about axis X1 in a first rotational direction, such as, for example, clockwise will translate screw 126 along axis X1 in a first axial direction, such as, for example, the direction shown by arrow A in FIG. 5 and rotation of screw 126 relative to core 38 about axis X1 in an opposite rotational direction, such as, for example, counterclockwise will translate screw 126 along axis X1 in an opposite section axial direction, such as, for example, the direction shown by arrow B in FIG. 5.

In some embodiments, body 124 is keyed to engage screw 126 such that translation of screw 126 relative to core 38 along axis X1 in the direction shown by arrow A in FIG. 5 also translates body 124 relative to core 38 along axis X1 in the direction shown by arrow A in FIG. 5 and translation of screw 126 relative to core 38 along axis X1 in the direction shown by arrow B in FIG. 5 also translates body 124 relative to core 38 along axis X1 in the direction shown by arrow B in FIG. 5. In some embodiments, screw 126 is coupled to body 124 by a pin. In some embodiments, screw 126 is coupled to body 124 by a collet. In some embodiments, screw 126 is coupled to body 124 by a snap ring. In some embodiments, screw 126 can be variously coupled to body 124, such as, for example, monolithic, integral connection, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts.

Body 124 includes an engagement portion 130 configured to engage screw 126 to couple screw 126 to body 124, as discussed herein. Body 124 includes an arm 132 that is connected to portion 130 by a transverse wall 134 and an arm 136 that is connected to portion 130 by a transverse wall 138. Arm 132 extends from wall 134 in a cantilevered configuration and arm 136 extends from wall 138 in a cantilevered configuration. Portion 130 includes an opening 140 configured for disposal of screw 126. Opening 140 defines a central longitudinal axis X2 and has a diameter d1. Arms 132, 136 each extend parallel to axis X2. In some embodiments, screw 126 includes a plurality of spaced apart splines 142 that are movable relative to one another to move a portion of screw 126 defined by splines 142 from a first configuration in which the portion of screw 126 defined by splines 142 has a first diameter such that splines 142 are spaced apart from portion 130 when the portion of screw 126 defined by splines 142 is positioned within opening 140 to a second configuration in which the portion of screw 126 defined by splines 142 has an increased second diameter such that splines 142 directly engage an inner surface of portion 130 that defines opening 140 when the portion of screw 126 defined by splines 142 is positioned within opening 140 to prevent screw 126 from translating relative to body 124 while allowing screw 126 to rotate relative to body 124. The portion of screw 126 defined by splines 142 is biased to the second configuration. That is, a force must be applied to splines 142 to move splines toward one another in order to move the portion of screw 126 defined by splines 142 from the second configuration to the first configuration.

Wall 134 includes an inclined surface 144 and an inclined surface 146 opposite surface 144. Arm 132 includes spaced apart extensions 148, 150 that extends from an inner surface of arm 132. Extension 148 includes an inclined surface 152 and an inclined surface 154 opposite surface 152. Extension 150 includes an inclined surface 156 and an inclined surface 158 opposite surface 156. Wall 138 includes an inclined surface 160 and an inclined surface 162 opposite surface 160. Arm 136 includes spaced apart extensions 164, 166 that extends from an inner surface of arm 136. Extension 164 includes an inclined surface 168 and an inclined surface 170 opposite surface 168. Extension 166 includes an inclined surface 172 and an inclined surface 174 opposite surface 172. Surfaces 144, 146, 152, 154, 158, 160, 162, 168, 170, 172, 174 are each angled relative to axis X2 and are configured to engage inclined surfaces of a bottom member or component, such as, for example, a plate 176 of implant 32 to selectively increase and decrease a height of implant 32 as member 122 translates relative to core 38 along axis X1, as discussed herein.

Screw 126 includes a socket 178 configured for disposal of a bit of a driver configured to rotate screw 126 relative to core 38 about axis X1 in opposite directions, as discussed herein. In some embodiments, socket 178 includes a hexalobe cross-sectional configuration configured for engagement with a bit of a driver having a hexalobe cross-sectional configuration to rotate screw 126. However, it is envisioned that socket 120 may include a square, triangular, polygonal, star cross sectional configuration configured engage a correspondingly shaped bit of a driver. Screw 126 includes a bore 180 that is coaxial with socket 178 and in communication with socket 178 such that an instrument can be positioned through socket 178 and bore 180 and into socket 120. As such, socket 178 and bore 180 are coaxial with socket 120 and bore 180 has a diameter that is equal to or greater than a diameter of socket 120. That is, socket 178 and bore 180 are coaxial with socket 120 when screw 106 is positioned within passageway 60 such that thread 108 engages thread 56 and screw 126 is positioned within passageway 62 such that thread 128 engages thread 58. In some embodiments, bore 180 is defined by inner surfaces of splines 142.

Figure 8:
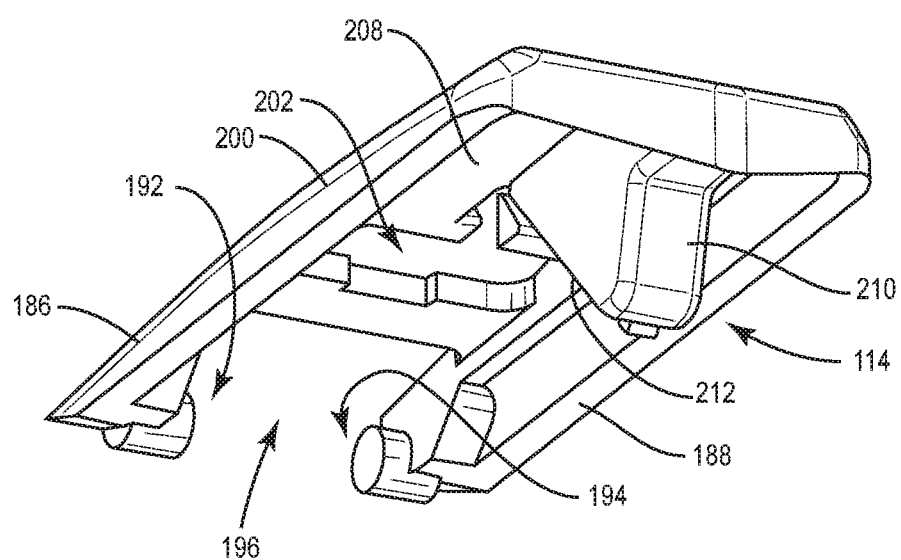
FIG. 8 is a perspective view of a component of the implant shown in FIG. 1.
Figure 9:
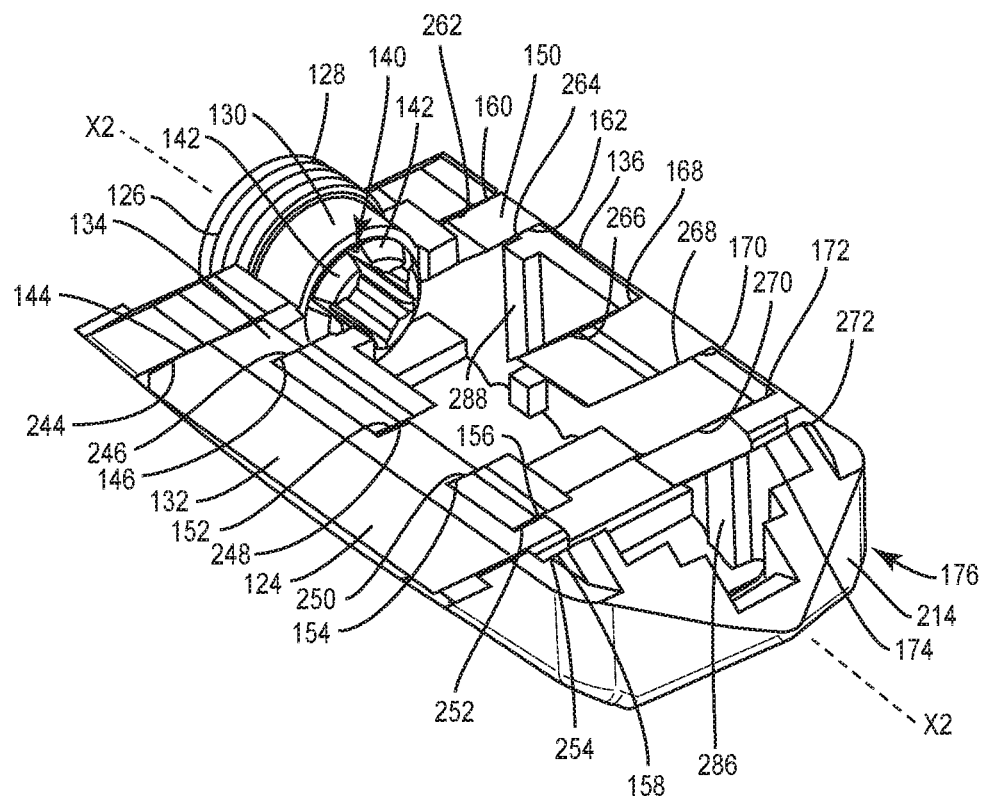
FIG. 9 is a perspective view of components of the implant shown in FIG. 1.
Figure 10:
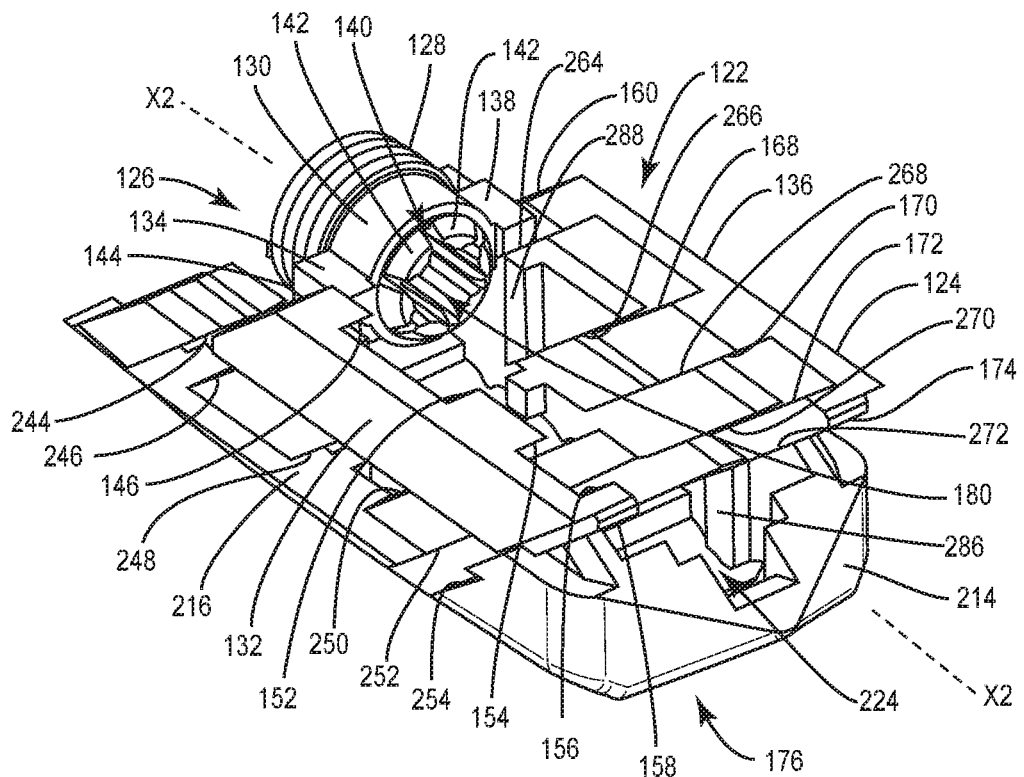
FIG. 10 is a perspective view of components of the implant shown in FIG. 1.
Figure 11:
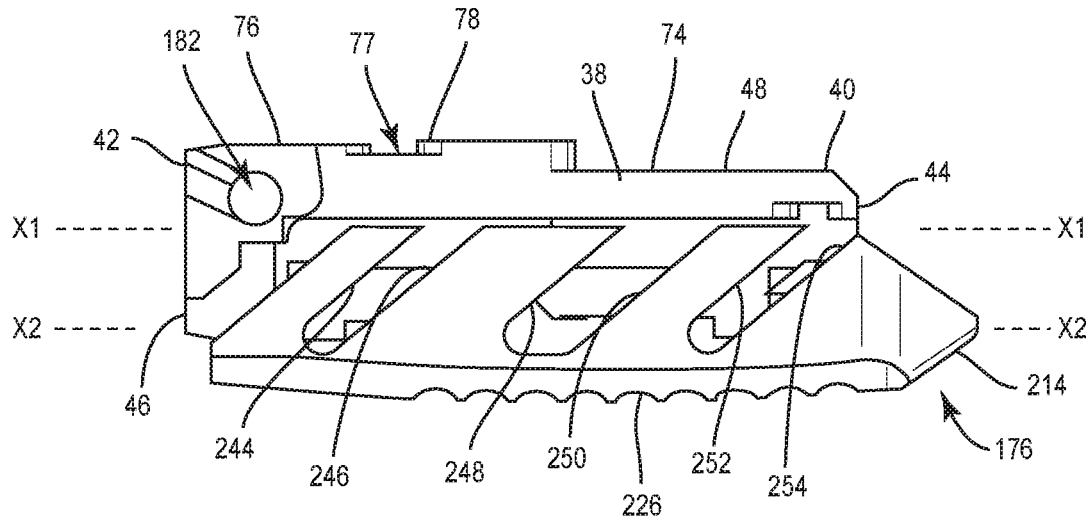
FIG. 11 is a side view of components of the implant shown in FIG. 1.

Plate 114 extends along a longitudinal axis X3 between an end 182 and an opposite end 184. End 182 slidingly engages body 104 and end 184 engages core 38 such that end 184 is pivotable or rotatable relative to core to selectively increase or decrease an angle of axis X3 relative to axis X1, as discussed herein. In some embodiments, core 38 includes a hole 182 that extends through walls 52, 54 and plate 114 includes a channel 184 that extends through spaced apart legs 186, 188 of plate 114 and is aligned with hole 182. A pin 190 extends through hole 182 and channel 184 such that plate 114 is rotatable relative to core 38 about pin 190. In some embodiments, plate 114 includes a cylindrical extension 192 extending from an inner surface of leg 186 and a cylindrical extension 194 extending from an inner surface of leg 188 such that extension 194 faces extension 192, as shown in FIG. 8. Extensions 192, 194 are configured for disposal in hole 182 such that plate 114 is rotatable relative to core 38 about extensions 192, 194.

Legs 186, 188 are spaced apart from one another by a gap 196. Gap 196 is configured to receive all or a portion of end 42 such that a vertebral engaging surface 198 of plate 114 is flush or substantially flush with a surface of end 42 when implant 32 is in a collapsed or non-expanded configuration, as shown in FIG. 1. Legs 186, 188 each extend outwardly from a body 200 of in a cantilevered configuration. Body 200 includes an aperture 202 configured to receive section 78 such that surface 198 is flush or substantially flush with a surface of section 78 when implant 32 is in a collapsed or non-expanded configuration, as shown in FIG. 1. Body 200 further includes spaced apart cavities 204, 206 each configured to receive a section of portion 74 such that surface 198 is flush or substantially flush with a surface of portion 74 when implant 32 is in a collapsed or non-expanded configuration, as shown in FIG. 1. In some embodiments, gap 196, aperture 202, cavity 204 and/or cavity 206 may have various cross section configurations, such as, for example, circular, oval, oblong, triangular, rectangular, square, polygonal, irregular, uniform, non-uniform, variable and/or tapered.

Plate 114 includes an inner surface 208 opposite surface 198 and a projection 210 that extends outwardly from surface 208. Projection 210 includes slot 118 and is configured for engagement with body 104 as member 102 translates relative to core 38 along axis X1 to rotate plate 114 relative to core 38 to selectively increase or decrease an angle of axis X3 relative to axis X1. In particular, projection 210 includes a surface defining a ramp 212 that extends at an angle β relative to axis X3. Slot 118 extends into ramp 212. In some embodiments, slot 118 extends at angle β relative to axis X3. In some embodiments, angle β is an acute angle. In some embodiments, angle β is an angle between about 1 degree and about 90 degrees. In some embodiments, angle β is an angle between about 1 degree and about 80 degrees. In some embodiments, angle β is an angle between about 1 degree and about 70 degrees. In some embodiments, angle β is an angle between about 1 degree and about 60 degrees. In some embodiments, angle β is an angle between about 1 degree and about 50 degrees. In some embodiments, angle β is an angle between about 1 degree and about 40 degrees. In some embodiments, angle β is an angle between about 1 degree and about 30 degrees. In some embodiments, angle β is an angle between about 1 degree and about 20 degrees. In some embodiments, angle β is an angle between about 1 degree and about 10 degrees. In some embodiments, slot 118 has a uniform width along an entire length of slot 118. In some embodiments, slot 118 is tapered toward aperture 202. In some embodiments, slot 118 is tapered away from aperture 202.

Figure 2:
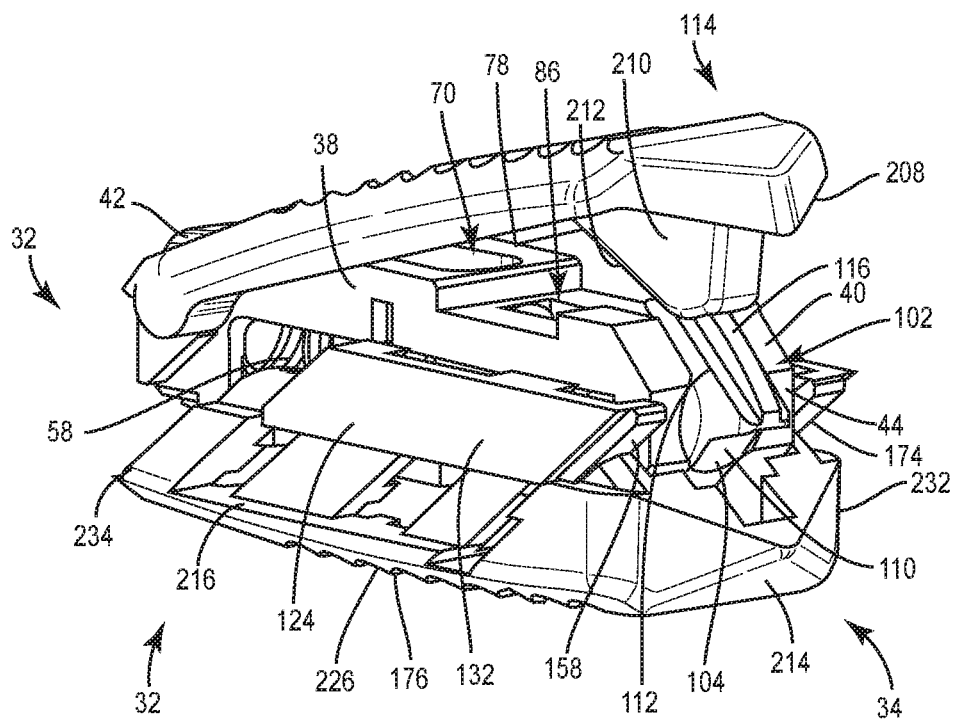
FIG. 2 is a perspective view of the implant shown in FIG. 1.
Figure 3:
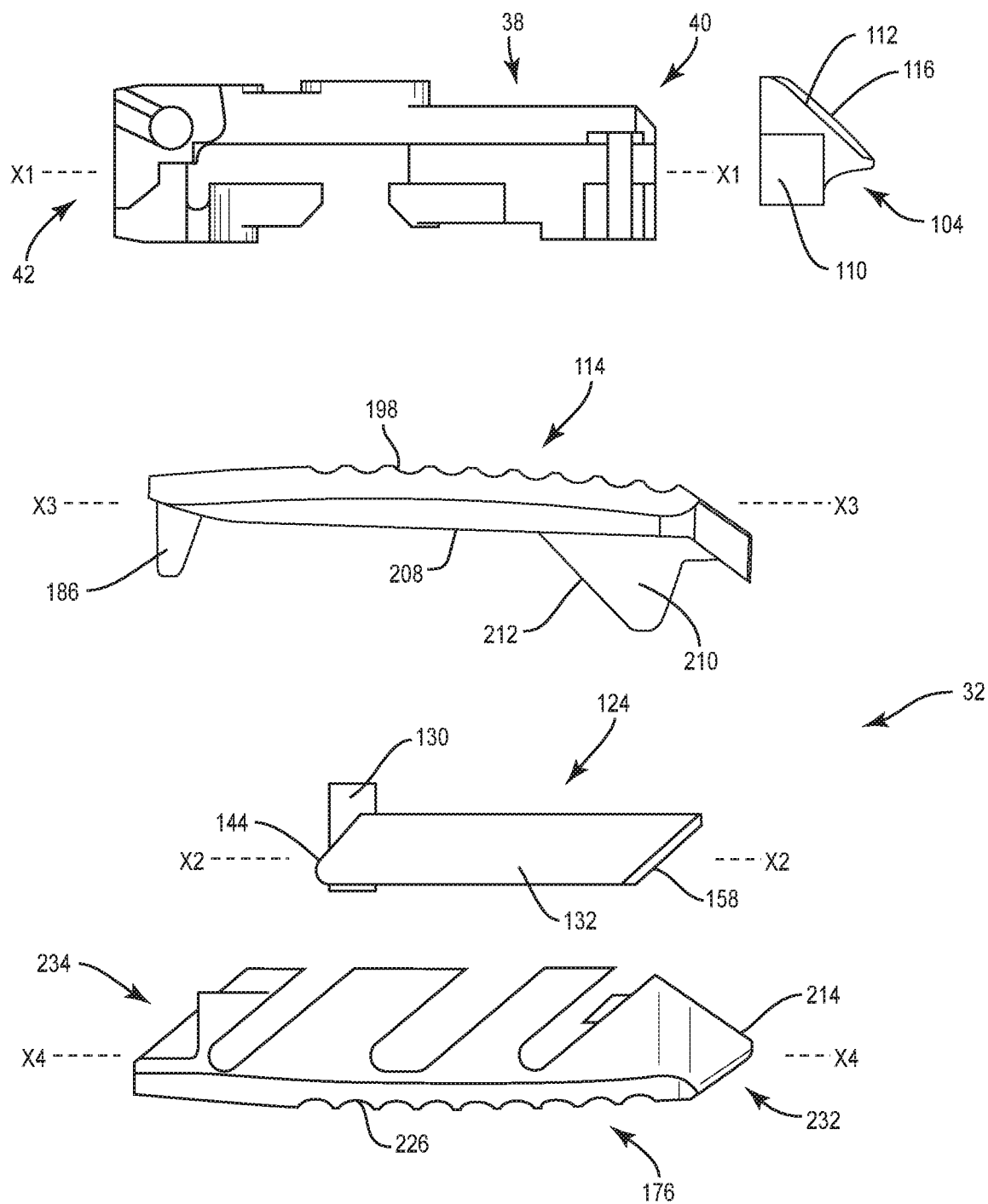
FIG. 3 is a side view of components of the implant shown in FIG. 1, with parts separated.
Figure 4:
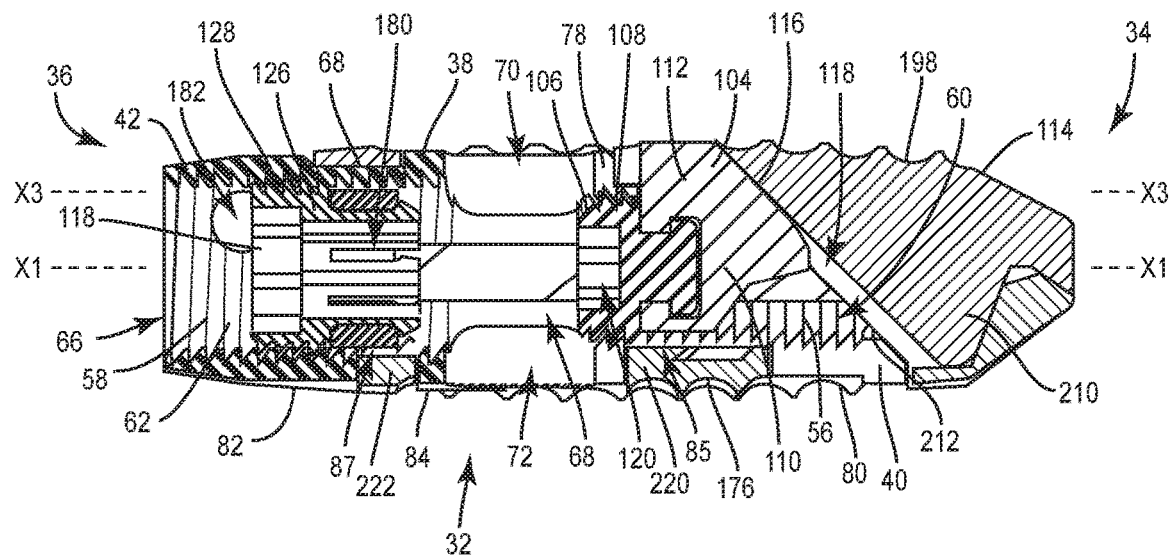
FIG. 4 is a side, cross-sectional view of the implant shown in FIG. 1.

As screw 106 translates relative to core 38 along axis X1 in the direction shown by arrow A in FIG. 5, body 104 also translates relative to core 38 along axis X1 in the direction shown by arrow A in FIG. 5 such that wall 112 slides along ramp 212 to pivot plate 114 relative to core 38 such that implant moves from a parallel configuration in which axis X3 extends parallel to axis X1, as shown in FIGS. 1 and 4, to a non-parallel configuration in which axis X3 extends at an angle γ relative to axis X1, as shown in FIGS. 2 and 5. In some embodiments, angle γ is an acute angle. In some embodiments, angle γ is an angle between about 1 degree and about 90 degrees. In some embodiments, angle γ is an angle between about 1 degree and about 80 degrees. In some embodiments, angle γ is an angle between about 1 degree and about 70 degrees. In some embodiments, angle γ is an angle between about 1 degree and about 60 degrees. In some embodiments, angle γ is an angle between about 1 degree and about 50 degrees. In some embodiments, angle γ is an angle between about 1 degree and about 40 degrees. In some embodiments, angle γ is an angle between about 1 degree and about 30 degrees. In some embodiments, angle γ is an angle between about 1 degree and about 20 degrees. In some embodiments, angle γ is an angle between about 1 degree and about 10 degrees. In some embodiments, surface 198 may be smooth, even and/or polished to prevent damage to tissue, or may be rough, textured, porous, semi-porous, dimpled, knurled, toothed and/or grooved to facilitate engagement with tissue.

Plate 176 includes an end wall 214 and rails 216, 218 that extend from wall 214 in an cantilevered configuration. Rail 216 is connected to rail 218 by a bridge 220 and a bridge 222 that is spaced apart from bridge 220. Rail 216 extends parallel to rail 218 and bridges 220, 222 extend perpendicular to rails 216, 218. Plate 176 includes a recess 224 between wall 214 and bridge 220. Recess 224 is configured to receive all or a portion of section 80 such that a vertebral engaging surface 226 of plate 176 is flush or substantially flush with a surface of section when implant 32 is in a collapsed or non-expanded configuration, as shown in FIG. 1. Plate 176 includes an aperture 228 between bridges 220, 222. Aperture 228 is configured to receive section 84 such that surface 226 is flush or substantially flush with a surface of section 84 when implant 32 is in a collapsed or non-expanded configuration, as shown in FIG. 1. Plate 176 further includes spaced apart a gap 230 that is defined by surfaces of bridge 222 and rails 216, 218. Gap 230 configured to receive section 82 such that surface 226 is flush or substantially flush with a surface of section 82 when implant 32 is in a collapsed or non-expanded configuration, as shown in FIG. 1. In some embodiments, gap 230, aperture 228 and/or recess 224 may have various cross section configurations, such as, for example, circular, oval, oblong, triangular, rectangular, square, polygonal, irregular, uniform, non-uniform, variable and/or tapered. In some embodiments, surface 226 may be smooth, even and/or polished to prevent damage to tissue, or may be rough, textured, porous, semi-porous, dimpled, knurled, toothed and/or grooved to facilitate engagement with tissue.

Plate 176 extends along a longitudinal axis X4 between an end 232 and an opposite end 234. Rails 216, 218 extend parallel to axis X4 and bridges 220, 222 extend perpendicular to axis X4. Plate 176 includes an inner surface 236 opposite surface 226. Rail 216 includes spaced apart extensions 238, 240, 242 that each extend outwardly from surface 236. Extension 238 includes an inclined surface 244. Extension 240 includes an inclined surface 246 and an inclined surface 248 opposite surface 246. Extension 240 includes an inclined surface 250 and an inclined surface 252 opposite surface 250. Wall 214 includes an inclined surface 254. Rail 218 includes spaced apart extensions 256, 258, 260 that each extend outwardly from surface 236. Extension 256 includes an inclined surface 262. Extension 258 includes an inclined surface 264 and an inclined surface 266 opposite surface 264. Extension 260 includes an inclined surface 268 and an inclined surface 270 opposite surface 268. Wall 214 includes an inclined surface 272.

Surfaces 144, 146, 152, 154, 158, 160, 162, 168, 170, 172, 174 are each angled relative to axis X4 and are configured to engage surfaces 144, 146, 152, 154, 158, 160, 162, 168, 170, 172, 174 to selectively increase and decrease a height of implant 32 as member 122 translates relative to core along axis X1. In particular, member 122 is coupled to plate 176 such that surface 244 engages surface 144, surface 246 engages surface 146, surface 248 engages surface 152, surface 250 engages surface 154, surface 252 engages surface 156, surface 254 engages surface 158, surface 262 engages surface 160, surface 264 engages surface 162, surface 266 engages surface 168, surface 268 engages surface 170, surface 270 engages surface 172 and surface 272 engages surface 174. Thread 128 engages thread 54 such that rotation of screw 126 relative to body 124 and core 38 in a first rotational direction, such as, for example, clockwise moves screw 126 and body 124 in the direction shown by arrow A in FIG. 5 such that surface 244 slides along surface 144, surface 246 slides along surface 146, surface 248 slides along surface 152, surface 250 slides along surface 154, surface 252 slides along surface 156, surface 254 slides along surface 158, surface 262 slides along surface 160, surface 264 slides along surface 162, surface 266 slides along surface 168, surface 268 slides along surface 170, surface 270 slides along surface 172 and surface 272 slides along surface 174 to increase a height of implant 32 either before or after the angle between axes X1, X3 is selectively increased or decreased. That is, the height of implant 32 can be increased by rotating screw 126 relative to body 124 and core 38 in the first rotational direction when axis X3 is parallel with axis X1 or when axis X3 is non-parallel with axis X1.

Rotation of screw 126 relative to body 124 and core 38 in an opposite second rotational direction, such as, for example, counterclockwise moves screw 126 and body 124 in the direction shown by arrow B in FIG. 5 such that surface 244 slides along surface 144, surface 246 slides along surface 146, surface 248 slides along surface 152, surface 250 slides along surface 154, surface 252 slides along surface 156, surface 254 slides along surface 158, surface 262 slides along surface 160, surface 264 slides along surface 162, surface 266 slides along surface 168, surface 268 slides along surface 170, surface 270 slides along surface 172 and surface 272 slides along surface 174 to decrease a height of implant 32 either before or after the angle between axes X1, X3 is selectively increased or decreased. That is, the height of implant 32 can be decreased by rotating screw 126 relative to body 124 and core 38 in the second rotational direction when axis X3 is parallel with axis X1 or when axis X3 is non-parallel with axis X1.

In some embodiments, rail 216 includes spaced apart rails, such as, for example, ribs 282, 284 and rail 218 includes spaced apart rails, such as, for example, ribs 286, 288. Ribs 282, 284, 286, 288 extend parallel to one another. In some embodiments, ribs 282, 284, 286, 288 each extend perpendicular to axis X4. Rib 282 is configured for disposal in groove 90. Rib 284 is configured for disposal in groove 94. Rib 286 is configured for disposal in groove 96. Rib 288 is configured for disposal in groove 100. As the height of implant 32 can is selectively increased or decreased by rotating screw 126 relative to body 124 and core 38 such that member 122 translates relative to core 38 along axis X1, rib 282 translates within groove 90, rib 284 translates within groove 94, rib 286 translates within groove 96 and rib 288 translates within groove 100. In some embodiments, rib 282, rib 284, rib 286 and/or rib 288 may be disposed at alternate orientations, relative to axis X4, such as, for example, transverse, and/or other angular orientations such as acute or obtuse, and/or may be offset or staggered.

Wherein the angle between axes X1, X3 has not been selectively increased or decreased such that axis X3 extends parallel to axis X1, the height of implant 32 may be selectively increased or decreased by rotating screw 126 relative to body 124 and core 38 such that implant increases or decreases from a first height defined by a distance from surface 198 to surface 226 to second height defined by the distance from surface 198 to surface 226, with axis X4 being parallel with axis X3 when implant 32 has the first height and the second height.

Alternatively, wherein the angle between axes X1, X3 has been selectively increased or decreased such that axis X3 extends non-parallel to axis X1, the height of implant 32 may be selectively increased or decreased by rotating screw 126 relative to body 124 and core 38 such that implant increases or decreases from a first height defined by a distance from surface 198 to surface 226 to second height defined by the distance from surface 198 to surface 226, with axis X4 being non-parallel with axis X3 when implant 32 has the first height and the second height.

Furthermore, it is envisioned that the angle between axes X1, X3 can be selectively increased or decreased such that axis X3 extends non-parallel to axis X1 after the height of implant 32 has been selectively increased or decreased with axis X4 being non-parallel with axis X3 when implant 32 has the first height and the second height. That is, axis X1 may extend parallel to axis X3 when prior to increasing or decreasing the height of the implant from the first height to the second height, and then after implant has been moved to have the second height, the angle between axes X1, X3 can be selectively increased or decreased, as discussed herein. This allows the height of implant 32 to be selectively increased or decreased before or after the angle between axes X1, X3 is selectively increased or decreased.

System 30 includes an instrument, such as, for example, an instrument 290 configured to control parallel expansion of implant 32 and angular expansion of implant 32 separately. Instrument 290 includes a sleeve 292 extending along a longitudinal axis X5 between an end 294 and an opposite end 296. Instrument 290 includes a shaft 298 including an end 300 and an opposite end 302 positioned within sleeve 292 such that end 302 is rotatable relative to sleeve 292 about axis X5 and is translatable relative to sleeve 292 along axis X5 in the direction shown by arrow C in FIG. 20 and the direction shown by arrow D in FIG. 20. Instrument 290 includes a shaft 304 including an end 306 and an opposite end 308 positioned within shaft 298 such that end 308 is rotatable relative to sleeve 292 and shaft 298 about axis X5 and is translatable relative to sleeve 292 and shaft 298 along axis X5 in the direction shown by arrow C in FIG. 20 and the direction shown by arrow D in FIG. 20. End 302 includes a bit 310 configured for disposal in socket 178 and end includes a bit 312 configured for disposal in socket 120. In some embodiments, bit 310 and/or bit 312 may include a hexalobe, square, triangular, polygonal, star cross sectional configuration or other configured mate with corresponding shape of socket 120 or socket 178.

To connect instrument 290 with implant 32, instrument 290 is positioned relative to implant 32 such that end 296 engages end 36. Shaft 298 is translated relative to sleeve 292 along axis X5 in the direction shown by arrow C in FIG. 20 such that end 308 moves through passageway 62 and bit 312 moves into socket 178. Shaft 304 is translated relative to shaft 298 along axis X5 in the direction shown by arrow C in FIG. 20 such that end 302 moves through passageway 62, bore 180 and passageway 60 and bit 310 moves into socket 120. It is noted that shaft 304 may be translated relative to shaft 298 along axis X5 in the direction shown by arrow C in FIG. 20 such that end 302 moves through passageway 62, bore 180 and passageway 60 and bit 310 moves into socket 120 before or after shaft 298 is translated relative to sleeve 292 along axis X5 in the direction shown by arrow C in FIG. 20 such that end 308 moves through passageway 62 bit 312 moves and into socket 178. In some embodiments, sleeve 212 and/or implant 32 include mating and/or locking features configured to couple sleeve 212 to implant 212 such that sleeve 212 is fixed relative to implant 32.

Once instrument 290 is coupled to implant 32 such that bit 310 is positioned in socket 120 and bit 312 is positioned in socket 178, shaft 304 may be rotated relative to shaft 298 about axis X5 in a first rotational direction such that member 102 moves relative to core 38 in the direction shown by arrow A in FIG. 5 and ramp 212 slides along wall 112 to increase an angle of implant 32 and/or move implant 32 from a configuration in which axis X3 extends parallel to axis X1, as shown in FIGS. 1 and 4, to a configuration in which axis X3 is non-parallel to axis X1 and/or extends at an angle relative to axis X1, as shown in FIGS. 2 and 5. The angle of implant 32 may be decreased and/or implant can be moved from the configuration in which axis X3 is non-parallel to axis X1 and/or extends at an angle relative to axis X1 to the configuration in which axis X3 extends parallel to axis X1 or at a decreased angle relative to axis X1, shaft 304 may be rotated relative to shaft 298 about axis X5 in an opposite section rotational direction such that member 102 moves relative to core 38 in the direction shown by arrow B in FIG. 5 and ramp 212 slides along wall 112.

Either before or after the angle of implant 32 is selectively increased or decreased, as discussed herein, shaft 298 may be rotated relative to sleeve 292 and shaft 304 about axis X5 in a first rotational direction such that member 122 moves relative to core 38 in the direction shown by arrow A in FIG. 5 and the inclined surfaces of member 122 slide along the inclined surfaces of plate 176 to increase a height of implant 32.

Alternatively, either before or after the angle of implant 32 is selectively increased or decreased, as discussed herein, and/or either before or after the height of implant has been selectively increased, as discussed herein, shaft 298 may be rotated relative to sleeve 292 and shaft 304 about axis X5 in an opposite rotational direction such that member 122 moves relative to core 38 in the direction shown by arrow B in FIG. 5 and the inclined surfaces of member 122 slide along the inclined surfaces of plate 176 to decrease a height of implant 32.

In operation and use, system 30 is employed with a surgical procedure, such as, a fusion treatment of a spine of a patient including vertebrae and body areas adjacent thereto, as discussed herein. System 30 may also be employed with other surgical procedures, such as, for example, discectomy, laminotomy, laminectomy, nerve root retraction, foramenotomy, facetectomy, decompression, and spinal, nucleus or disc replacement.

For example, system 30 can be employed with a surgical arthrodesis procedure, such as, for example, an interbody fusion for treatment of an applicable condition or injury of an affected section of a spinal column and adjacent areas within a body, such as, for example, an intervertebral disc space between a first vertebra and a second vertebra. It is contemplated that intervertebral implant 32 of system 30, described above, can be inserted within the intervertebral disc space to space apart articular joint surfaces, provide support and maximize stabilization of the vertebrae. It is further contemplated that intervertebral implant 32 provides height restoration between vertebral bodies, decompression, restoration of sagittal balance and/or resistance of subsidence into vertebral endplates.

In use, to treat the affected section of the vertebrae, a medical practitioner obtains access to a surgical site including the vertebrae in any appropriate manner, such as through incision and retraction of tissues. It is envisioned that system 30 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure is performed for treating the spine disorder. Intervertebral implant 32, described above, is then employed to augment the surgical treatment. Intervertebral implant 32 can be delivered or implanted as a pre-assembled device or can be assembled in situ. Intervertebral implant 32 can be completely or partially revised, removed or replaced in situ. It is contemplated that one or all of the components of the interbody implant system can be delivered to the surgical site via manual manipulation and/or a free hand technique. It is further contemplated that intervertebral implant 32 may be inserted posteriorly, and then manipulated anteriorly and/or lateral and/or medial.

An incision is made in the body of a patient and a cutting instrument creates a surgical pathway for implantation of intervertebral implant 32 within the patient body. A guide instrument is employed to initially distract the first vertebra from the second vertebra. A sleeve or cannula is used to access the intervertebral disc space and facilitate delivery and access for components of the interbody implant system. A preparation instrument can be inserted within the sleeve or cannula and disposed within the intervertebral disc space. The preparation instrument(s) can be employed to remove some or all of the disc tissue including the disc nucleus and fluids, adjacent tissues and/or bone, corticate, scrape and/or remove tissue from the surfaces of endplates of the first and second vertebrae, as well as for aspiration and irrigation of the region according to the requirements of a particular surgical application.

Figure 20:
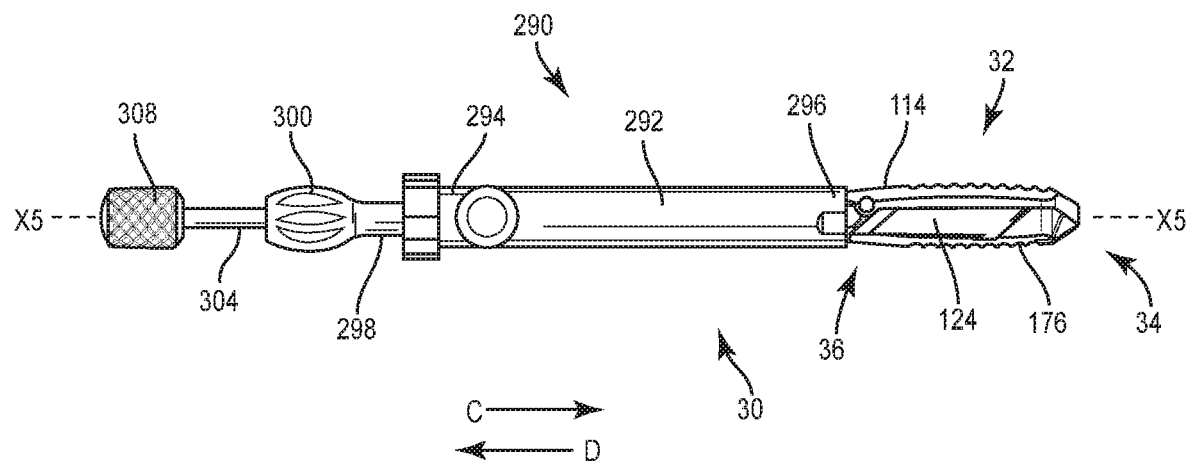
FIG. 20 is a side view of the implant shown in FIG. 1 coupled to of an instrument of a system in accordance with the principles of the present disclosure.

Intervertebral implant 32 is coupled to instrument 290, as discussed above, and implant 32 is inserted into the patient using instrument 290 with implant 32 disposed in an undeployed or unexpanded configuration, as shown in FIG. 20. Implant 32 is delivered along the surgical pathway using a substantially posterior approach to position implant 32 within the intervertebral disc space.

Figure 21:
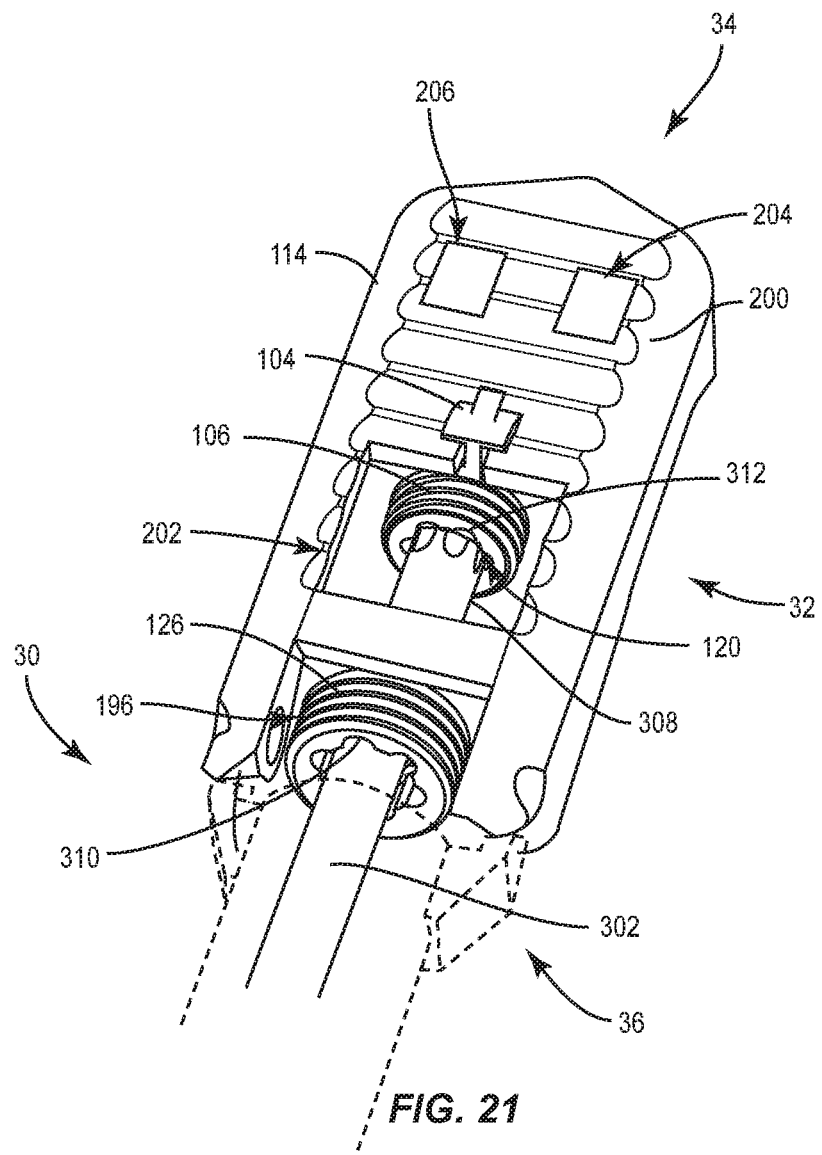
FIG. 21 is a perspective view, in part phantom, of the implant shown in FIG. 1 coupled to the instrument shown in FIG. 20.
Figure 22:
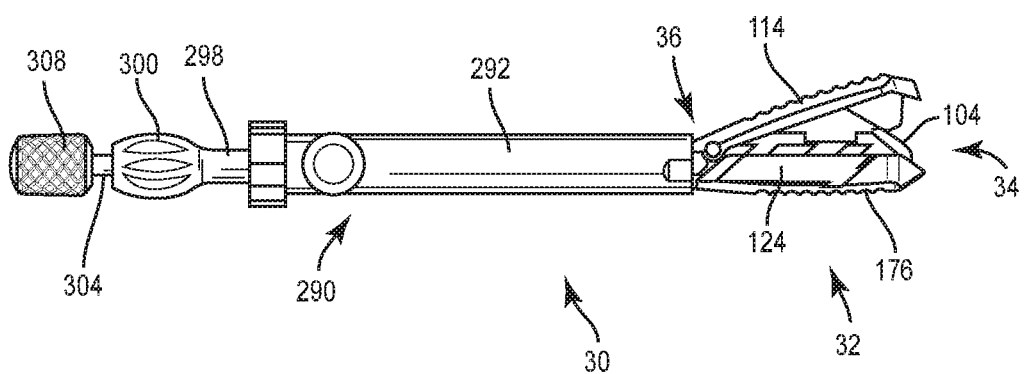
FIG. 22 is a side view of the implant shown in FIG. 1 coupled to the instrument shown in FIG. 20.

Upon desired positioning of intervertebral implant 32 within the intervertebral disc space, implant 32 is deployed within the intervertebral disc space to move implant 32 from the undeployed or unexpanded configuration, shown in FIGS. 20 and 21, to a first deployed or expanded configuration, shown in FIG. 22, in which the angle of implant 32 is increased by rotating shaft 304 relative to shaft 298 about axis X5 in a first rotational direction such that member 102 moves relative to core 38 in the direction shown by arrow A in FIG. 5 and ramp 212 slides along wall 112. That is, implant 32 moves from a configuration in which axis X3 extends parallel to axis X1, as shown in FIGS. 1 and 4, to a configuration in which axis X3 is non-parallel to axis X1 and/or extends at an angle relative to axis X1, as shown in FIGS. 2 and 5. The angle of implant 32 may be decreased and/or implant can be moved from the configuration in which axis X3 is non-parallel to axis X1 and/or extends at an angle relative to axis X1 to the configuration in which axis X3 extends parallel to axis X1 or at a decreased angle relative to axis X1, shaft 304 may be rotated relative to shaft 298 about axis X5 in an opposite second rotational direction such that member 102 moves relative to core 38 in the direction shown by arrow B in FIG. 5 and ramp 212 slides along wall 112.

Figure 23:
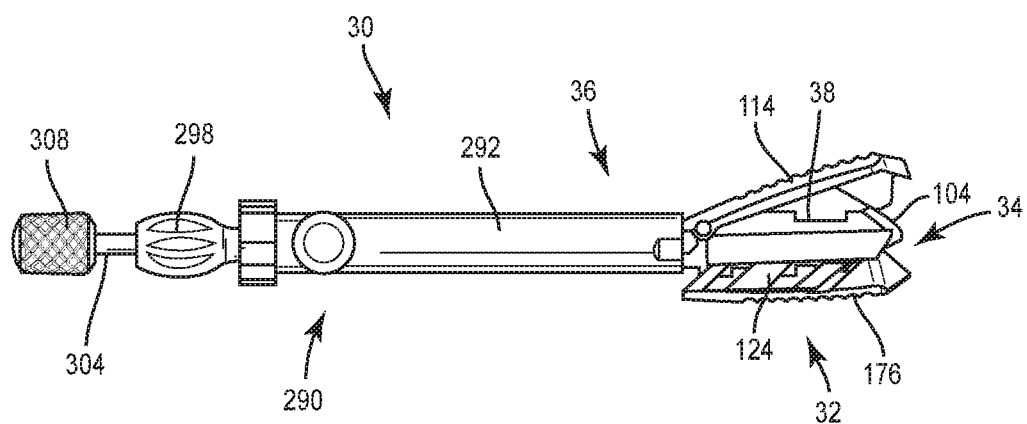
FIG. 23 is a side view of the implant shown in FIG. 1 coupled to the instrument shown in FIG. 20.

In some embodiments, implant 32 is moved from the first deployed or expanded configuration, shown in FIG. 22, to a second deployed or expanded configuration, shown in FIG. 23, in which the height of implant 32 is increased by rotating shaft 298 relative to sleeve 292 and shaft 304 about axis X5 in a first rotational direction such that member 122 moves relative to core 38 in the direction shown by arrow A in FIG. 5 and the inclined surfaces of member 122 slide along the inclined surfaces of plate 176. Alternatively, implant 32 can be moved from the first deployed or expanded configuration, shown in FIG. 22, to a third deployed or expanded configuration in which the height of implant 32 is decreased by rotating shaft 298 relative to sleeve 292 and shaft 304 about axis X5 in an opposite rotational direction such that member 122 moves relative to core 38 in the direction shown by arrow B in FIG. 5 and the inclined surfaces of member 122 slide along the inclined surfaces of plate 176. However, as discussed herein, the height of implant 32 may be selectively increased and/or decreased before or after the angle of implant 32 is selectively increased or decreased.

In some embodiments, intervertebral implant 32 can be expanded from the undeployed or unexpanded configuration to alternate configurations between the undeployed or unexpanded configuration and the first deployed or expanded configuration, to expand intervertebral implant 32 as may be desired. In some embodiments, intervertebral implant 32 can be expanded from the first deployed or expanded configuration to alternate configurations between the first deployed or expanded configuration and the second deployed or unexpanded configuration, to expand intervertebral implant 32 as may be desired.

As implant 32 moves from the undeployed or unexpanded configuration to the first and/or second deployed or expanded configuration, surface 198 moves away from surface 226 such that surfaces 198, 226 push against the vertebrae to move the first vertebra away from the second vertebra and increase the size of the intervertebral disc space. It is contemplated that in the first and/or second deployed or expanded configuration, intervertebral implant 32 provides height restoration between the first vertebra and the second vertebrae, decompression, restoration of sagittal balance and resistance of subsidence into the endplates of the vertebrae. Implant 32 may be kept in the first and/or second deployed or expanded configuration to maintain the increased size of the intervertebral disc space. In some embodiments, a material, such as, for example, bone graft is positioned within cavity 68, aperture 70 and/or aperture 72 to promote bone growth to fuse the first vertebra with the second vertebra. In some embodiments, implant 32 may be moved directly from the undeployed or unexpanded configuration to the second deployed or expanded configuration such that engagement surface 198 extends parallel to engagement surface 226 when implant 32 is in the second deployed or expanded configuration within the disc space to push the vertebrae apart without increasing or decreasing the angle of implant 32. In some embodiments, implant 32 may be moved from the second deployed or expanded configuration to the first deployed or expanded configuration after implant 32 pushes the vertebrae apart.

In some embodiments, the bone graft can be a particulate material, which may include an osteoconductive material such as HA and/or an osteoinductive agent such as a bone morphogenic protein (BMP) to enhance bony fixation of intervertebral implant 32 with the adjacent vertebrae. It is contemplated that the bone graft may include therapeutic polynucleotides or polypeptides. It is further contemplated that the agent and/or bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Intervertebral implant 32 can be made of radiolucent materials such as polymers. Radiomarkers may be included for identification under x-ray, fluoroscopy, CT or other imaging techniques. It is envisioned that the bone graft may include one or a plurality of therapeutic agents and/or pharmacological agents for release, including sustained release, to treat, for example, pain, inflammation and degeneration.

It is envisioned that the components of system 30, which may include one or a plurality of intervertebral implants 32, can be delivered to the surgical site via alternate approaches. In one embodiment, intervertebral implant 32 is delivered through the surgical pathway along a transforaminal lumbar interbody fusion approach into the intervertebral disc space and disposed in the deployed or expanded configuration. In one embodiment, a plurality of intervertebral implants 32 are delivered through the surgical pathway along a posterior lumbar interbody fusion approach into the intervertebral disc space and disposed in the deployed or expanded configuration in a side by side orientation.

In some embodiments, intervertebral implant 32 can be collapsed from the second deployed or expanded configuration to alternate configurations between the second deployed or expanded configuration and the first deployed or expanded configuration, to collapse intervertebral implant 32 as may be desired to reposition with or remove intervertebral implant 32 from the intervertebral disc space. In some embodiments, intervertebral implant 32 can be collapsed from the first deployed or expanded configuration to alternate configurations between the first deployed or expanded configuration and the undeployed or unexpanded configuration, to collapse intervertebral implant 32 as may be desired to reposition with or remove intervertebral implant 32 from the intervertebral disc space.

Implant 32 may be moved from the first and/or second deployed or expanded configuration to the undeployed or unexpanded configuration. Once implant 32 is in the undeployed or unexpanded configuration, implant 32 can be moved within the intervertebral disc space and/or removed from the intervertebral disc space, as desired.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A device to space apart vertebral members, the device comprising:
   a core extending along a longitudinal axis between opposite proximal and distal ends, the core defining a first female thread and a second female thread, the first female thread having a major diameter that is less than a major diameter of the second female thread;
   a first member comprising a first body and a first drive screw coupled to the first body, the first drive screw having a first male thread configured to engage the first female thread;
   a second member comprising a second body and a second drive screw coupled to the second body, the second drive screw being coaxial with the first drive screw, the second drive screw having a second male thread configured to engage the second female thread;

a first plate coupled to the core and the first body, the first plate comprising a first vertebral engaging surface;

a pin extending through the first plate and the core such that the first plate is pivotable relative to the core about the pin; and a second plate coupled to the core and the second body, the second plate comprising a second vertebral engaging surface, wherein the drive screws are configured to independently rotate relative to the core to pivot the first plate relative to the core and to alter a distance between the first vertebral engaging surface and the second vertebral engaging surface.

2. The device recited in claim 1, wherein rotation of first drive screw relative to the core in a first rotational direction translates the first body along the longitudinal axis in a first direction such that the first plate pivots relative to the core to move the device from a first orientation in which the first vertebral engaging surface extends parallel to the longitudinal axis and the second vertebral engaging surface to a second orientation in which the first vertebral engaging surface extends at an acute angle relative to the longitudinal axis and the second vertebral engaging surface.

3. The device recited in claim 2, wherein rotation of the first drive screw relative to the core in an opposite second rotational direction translates the first body along the longitudinal axis in an opposite second direction such that the first plate pivots relative to the body to move the device from the second orientation to the first orientation.

4. The device recited in claim 1, wherein rotation of second drive screw relative to the core in a first rotational direction translates the second body relative to the core along the longitudinal axis in a first longitudinal direction to move the device from a first configuration in which the vertebral engaging surfaces are spaced apart a first distance from one another to a second configuration in which the vertebral engaging surfaces are spaced apart a second distance from one another, the second distance being greater than the first distance.

5. The device recited in claim 4, wherein the second body comprises inclined surfaces that slide along inclined surfaces of the second plate as the second body translates relative to the core along the longitudinal axis to move the device from the first configuration to the second configuration.

6. The device recited in claim 4, wherein rotation of the second drive screw relative to the core in an opposite second rotational direction translates the second body along the longitudinal axis in an opposite second longitudinal direction to move the device from the second configuration to the first configuration.

7. The device recited in claim 4, wherein the vertebral engaging surfaces are parallel to one another as the device moves between the first configuration and the second configuration.

8. The device recited in claim 4, wherein the second plate comprises a plurality of rails each extending perpendicular to the longitudinal axis and the core comprises a plurality of slots each extending perpendicular to the longitudinal axis, the rails each translating within one of the slots as the device moves between the first configuration and the second configuration.

9. The device recited in claim 1, wherein:

rotation of first drive screw relative to the core translates the first body along the longitudinal axis such that the first plate pivots relative to the core to move the device from a first orientation in which the first vertebral engaging surface extends parallel to the longitudinal axis and the second vertebral engaging surface to a second orientation in which the first vertebral engaging surface extends at an acute angle relative to the longitudinal axis and the second vertebral engaging surface; and rotation of second drive screw relative to the core in a first rotational direction translates the second body relative to the core along the longitudinal axis in a first longitudinal direction to move the device from a first configuration in which the vertebral engaging surfaces are spaced apart a first distance from one another to a second configuration in which the vertebral engaging surfaces are spaced apart a second distance from one another, the second distance being greater than the first distance.

10. The device recited in claim 1, wherein the first female thread is spaced apart from the second female thread.

11. The device recited in claim 1, wherein the first female thread is spaced apart from the second female thread by a gap, a portion of the second drive screw being configured for positioning in the gap.

12. The device recited in claim 1, wherein the second drive screw comprises a bore that is coaxial with a central longitudinal axis defined by the first drive screw such that an instrument can be positioned through the bore and into a socket of the first drive screw.

13. The device recited in claim 1, wherein the first plate comprises an inner surface opposite the first vertebral engaging surface, the first plate comprising a flange extending outwardly from the inner surface, the flange including a groove, the first body including a projection that is movably disposed in the groove as the first plate pivots relative to the core.

14. The device recited in claim 1, wherein the first plate comprises a body that includes the first vertebral engaging surface, the body of the first plate comprising spaced apart cylindrical extensions, the core comprising spaced apart openings each configured for disposal of one of the extensions such that such that the first plate is pivotable relative to the core about the extensions.

15. The device recited in claim 1, wherein the second body includes a collar defining an opening, the second drive screw comprising a first portion and a second portion, the first portion comprising the second male thread, the second portion comprising a plurality of spaced apart splines that define a collet, the collet being positioned within the opening to prevent the second body from translating relative to the second drive screw as the second drive screw rotates relative to the core.

16. A device to space apart vertebral members, the device comprising:

a core extending along a longitudinal axis between opposite proximal and distal ends, the core defining a first female thread and a second female thread that is spaced apart from the first female thread, the first female thread having a major diameter that is less than a major diameter of the second female thread;

a first member comprising a first body and a first drive screw coupled to the first body, the first drive screw having a first male thread configured to engage the first female thread;

a second member comprising a second body and a second drive screw coupled to the second body, the second drive screw having a second male thread configured to engage the second female thread, the first drive screw being coaxial with the second drive screw such that a bore of the second drive screw is in communication with a socket of the first drive screw, the second drive screw comprising a bore that is coaxial with a central longitudinal axis defined by the first drive screw such that an instrument can be positioned through the bore and into a socket of the first drive screw;

a first plate coupled to the core and the first body, the first plate comprising a first vertebral engaging surface; and a second plate coupled to the core and the second body, the second plate comprising a second vertebral engaging surface, wherein the drive screws are configured to independently rotate relative to the core to pivot the first plate relative to the core and to alter a distance between the first vertebral engaging surface and the second vertebral engaging surface, wherein rotation of first drive screw relative to the core translates the first body along the longitudinal axis such that the first plate pivots relative to the core to move the device from a first orientation in which the first vertebral engaging surface extends parallel to the longitudinal axis and the second vertebral engaging surface to a second orientation in which the first vertebral engaging surface extends at an acute angle relative to the longitudinal axis and the second vertebral engaging surface, wherein rotation of the first drive screw relative to the core in an opposite second rotational direction translates the first body along the longitudinal axis in an opposite second direction such that the first plate pivots relative to the body to move the device from the second orientation to the first orientation, wherein the second body comprises inclined surfaces that slide along inclined surfaces of the second plate as the second body translates relative to the core along the longitudinal axis to move the device from the first configuration to the second configuration, wherein the second plate comprises a plurality of rails each extending perpendicular to the longitudinal axis and the core comprises a plurality of slots each extending perpendicular to the longitudinal axis, the rails each translating within one of the slots as the device moves between the first configuration and the second configuration, wherein rotation of second drive screw relative to the core in a first rotational direction translates the second body relative to the core along the longitudinal axis in a first longitudinal direction to move the device from a first configuration in which the vertebral engaging surfaces are spaced apart a first distance from one another to a second configuration in which the vertebral engaging surfaces are spaced apart a second distance from one another, the second distance being greater than the first distance, and wherein rotation of the second drive screw relative to the core in an opposite second rotational direction translates the second body along the longitudinal axis in an opposite second longitudinal direction to move the device from the second configuration to the first configuration.

17. The device recited in claim 1, wherein the second body is movable relative to the first body.

18. The device recited in claim 1, wherein the second body includes spaced apart arms, the first body being movably positioned between the arms.

19. A device to space apart vertebral members, the device comprising:

a monolithic core extending along a longitudinal axis between opposite proximal and distal ends, the core defining a first female thread and a second female thread;

a first member comprising a first body and a first drive screw coupled to the first body, the first drive screw having a first male thread configured to engage the first female thread;

a second member comprising a second body and a second drive screw coupled to the second body, the second drive screw being coaxial with the first drive screw, the second drive screw having a second male thread configured to engage the second female thread;

a first plate coupled to the core and the first body, the first plate comprising a first vertebral engaging surface;

a pin extending through the first plate and the core such that the first plate is pivotable relative to the core about the pin; and a second plate coupled to the core and the second body, the second plate comprising a second vertebral engaging surface, wherein the drive screws are configured to independently rotate relative to the core to pivot the first plate relative to the core and to alter a distance between the first vertebral engaging surface and the second vertebral engaging surface, and wherein the second drive screw comprises a bore that is coaxial with a central longitudinal axis defined by the first drive screw such that an instrument can be positioned through the bore and into a socket of the first drive screw.

* * * * *